US009850527B2

(12) United States Patent
Too et al.

(10) Patent No.: US 9,850,527 B2
(45) Date of Patent: Dec. 26, 2017

(54) MODIFIED STEM-LOOP OLIGONUCLEOTIDE MEDIATED REVERSE TRANSCRIPTION AND BASE-SPACING CONSTRAINED QUANTITATIVE PCR

(75) Inventors: Heng Phon Too, Singapore (SG); Azlinda B. Anwar, Singapore (SG)

(73) Assignee: National University of Singapore, Singapore (SG)

( * ) Notice: Subject to any disclaimer, the term of this patent is extended or adjusted under 35 U.S.C. 154(b) by 777 days.

(21) Appl. No.: 13/704,482

(22) PCT Filed: Jun. 13, 2011

(86) PCT No.: PCT/SG2011/000210
§ 371 (c)(1),
(2), (4) Date: Mar. 27, 2013

(87) PCT Pub. No.: WO2011/159256
PCT Pub. Date: Dec. 22, 2011

(65) Prior Publication Data
US 2013/0177915 A1    Jul. 11, 2013

Related U.S. Application Data

(60) Provisional application No. 61/354,683, filed on Jun. 14, 2010.

(51) Int. Cl.
*C12Q 1/68*    (2006.01)

(52) U.S. Cl.
CPC ......... *C12Q 1/6853* (2013.01); *C12Q 1/6844* (2013.01); *C12Q 1/6846* (2013.01); *C12Q 2600/178* (2013.01)

(58) Field of Classification Search
None
See application file for complete search history.

(56) References Cited

U.S. PATENT DOCUMENTS

| 6,027,891 A | 2/2000 | Von Knebel-Döberitz et al. |
| 2007/0054287 A1 | 3/2007 | Bloch et al. |
| 2007/0077570 A1* | 4/2007 | Lao et al. .......... 435/6 |
| 2007/0111226 A1* | 5/2007 | Tan ............ C12Q 1/6851 435/6.14 |

FOREIGN PATENT DOCUMENTS

| JP | 2001-513623 A | 9/2001 |
| JP | 2004-532615 A | 10/2004 |
| JP | 2006-506978 A | 3/2006 |
| WO | WO 98/02449 A1 | 1/1998 |
| WO | WO 02/057479 A2 | 7/2002 |
| WO | WO 2004/022748 | 3/2004 |
| WO | WO 2004/022784 | 3/2004 |
| WO | WO 2004022784 A2 * | 3/2004 |
| WO | WO 2007/025281 | 3/2007 |
| WO | WO 2009/135093 | 11/2009 |
| WO | WO 2011/159256 A1 | 12/2011 |

OTHER PUBLICATIONS

Office Action, dated Aug. 6, 2014, from corresponding Chinese patent application No. 201180038333.8.
Wan et al., "High-performance quantification of mature microRNAs by real-time RT-PCR using deoxyuridine-incorporated oligonucleotides and hemi-nested primers," RNA, Jul. 2010, pp. 1436-1445, vol. 16, issue 7.
Chinese Office Action dated Dec. 12, 2014 for Application No. CN2011800383338.
Office Action, dated Dec. 30, 2013, for Chinese Application No. 201180038333.8.
Supplementary European Search Report, dated Oct. 23, 2013, for European Application No. EP11796068.2.
International Search Report and Written Opinion, dated Sep. 7, 2011 for International Application No. PCT/SG2011/000210.
International Preliminary Report on Patentability, dated Dec. 27, 2012 for International Application No. PCT/SG2011/000210.
Ambros et al., MicroRNAs and other tiny endogenous RNAs in C. elegans. Curr Biol, 2003, 13:807-818.
Anwar et al., A stem-loop-mediated reverse transcription realtime PCR for the selective detection and quantification of the replicative strand of an RNA virus, Anal Biochem., 2006, 352:120-128.
Bar et al., MicroRNA discovery and profiling in human embryonic stem cells by deep sequencing of small RNA libraries, Stem Cells, 2008, 26:2496-2505.
Bartel, MicroRNAs: genomics, biogenesis, mechanism, and function, Cell, 2004, 116:281-297.
Bartel, MicroRNAs: target recognition and regulatory functions, Cell, 2009, 136:215-233.
Bissels et al., Absolute quantification of microRNAs by using a universal reference, RNA Society, 2009, 15:2375-2384.
Calin et al., MicroRNA profiling reveals distinct signatures in B cell chronic lymphocytic leukemias, Proc Natl Acad Sci USA, 2004, 101:11755-11760.
Carthew, Gene regulation by microRNAs, Curr Opin Genet Dev, 2006, 16:203-208.
Chen et al., Characterization of microRNAs in serum: a novel class of biomarkers for diagnosis of cancer and other diseases, Cell Res, 2008, 18:997-1006.
Chen et al., microRNAs and muscle disorders, J Cell Sci, 2009, 122:13-20.
Chen et al., Realtime quantification of microRNAs by stem-loop RT-PCR., Nucleic Acids Res, 2005, 33:e179.

(Continued)

*Primary Examiner* — Prabha Chunduru
(74) *Attorney, Agent, or Firm* — Wolf, Greenfield & Sacks, P.C.

(57) ABSTRACT

There is provided a method for detecting a target RNA molecule in a sample comprising reverse transcription, amplification of the reverse transcription product, and detection of the amplification product, involving the use of (i) an RT oligonucleotide comprising a stem-loop portion containing one or more nucleotides modified or modifiable to block DNA polymerase extension and a target annealing portion that is complementary to a downstream portion of the target RNA, the target annealing portion located 3' to the stem-loop portion, (ii) a first amplification primer that anneals to a downstream portion of a 3' extended region of the reverse transcription product and (ii) a second amplification primer that anneals to an interface portion of a DNA strand complementary to the reverse transcription product, the interface portion comprising a region that is complementary to a 3' portion of the RT oligonucleotide and a 5' portion of the 3' extended region in the reverse transcription product.

19 Claims, 26 Drawing Sheets

(56) References Cited

OTHER PUBLICATIONS

Chen et al., Reproducibility of quantitative RT-PCR array in miRNA expression profiling and comparison with microarray analysis, BMC Genomics, 2009, 10:407.
Cheng et al., Highly sensitive determination of microRNA using target-primed and branched rolling-circle amplification, Angew Chem. 2009, 121:3318-3322.
Childs et al., Lowlevel expression of microRNAs let-7d and miR-205 are prognostic markers of head and neck squamous cell carcinoma, Am J Pathol, 2009, 174:736-745.
Duncan et al., Absolute quantitation of microRNAs with a PCR-based assay, Anal Biochem, 2006, 359:268-270.
Friedman et al., Most mammalian mRNAs are conserved targets of microRNAs, Genome Res, 2009, 19:92-105.
Goff et al., Ago2 immunoprecipitation identifies predicted microRNAs in human embryonic stem cells and neural precursors, PLoS One, 2009, 4:e7192.
Griffiths-Jones et al., miRBase: tools for microRNA genomics, Nucleic Acids Res, 2008, 36:D154-158.
Harfe, MicroRNAs in vertebrate development, Curr Opin Genet Dev, 2005, 15:410-415.
Hebert et al., Alterations of the microRNA network cause neurodegenerative disease, Trends Neurosci, 2009, 32:199-206.
Hunt et al., Direct detection and quantification of microRNAs, Anal Biochem, 2009, 387:1-12.
Jiang et al., Real-time expression profiling of microRNA precursors in human cancer cell lines, Nucleic Acids Res, 2005, 33:5394-5403.
Lawler et al., Emerging functions of microRNAs in glioblastoma, J Neurooncol, 2009, 92:297-306.
Lewis et al., Conserved seed pairing, often flanked by adenosines, indicates that thousands of human genes are microRNA targets, Cell, 2005, 120:15-20.
Li et al., MicroRNA-21 targets LRRFIP1 and contributes to VM-26 resistance in glioblastoma multiforme, Brain Res, 2009, 1286:13-18.
Lindahl et al., DNA N-glycosidases: properties of uracil-DNA glycosidase from *Escherichia coli*. J Biol Chem, 1977, 252:3286-3294.
Lindsay, microRNAs and the immune response, Trends Immunol, 2008, 29:343-351.
Longo et al., Use of uracil DNA glycosylase to control carry-over contamination in polymerase chain reactions, Gene, 1990, 93:125-128.
Mendes et al., Current tools for the identification of miRNA genes and their targets. Nucleic Acids Res, 2009, 37:2419-2433.
Mestdagh et al., High-throughput stem-loop RT-qPCR miRNA expression profiling using minute amounts of input RNA, Nucleic Acids Res, 2008, 36:e143.
Michael et al., Reduced accumulation of specific microRNAs in colorectal neoplasia, Mol Cancer Res, 2003, 1:882-891.
Miska, How microRNAs control cell division, differentiation and death, Curr Opin Genet Dev, 2005, 15:563-568.
Mitchell et al., Circulating microRNAs as stable blood-based markers for cancer detection, Proc Natl Acad Sci U S A, 2008, 105:10513-10518.
Nishino et al., Hmga2 promotes neural stem cell self-renewal in young but not old mice by reducing p16Ink4a and p19Arf Expression, Cell, 2008, 135:227-239.
Pang et al., Oncogenic role of microRNAs in brain tumors, Acta Neuropathol, 2009, 117:599-611.
Raymond et al., Simple, quantitative primer-extension PCR assay for direct monitoring of microRNAs and short-interfering RNAs, RNA, 2005, 11:1737-1744.
Schmittgen et al., A high-throughput method to monitor the expression of microRNA precursors, Nucleic Acids Res, 2004, 32:e43.
Schmittgen et al., Realtime PCR quantification of precursor and mature microRNA, Methods, 2008, 44:31-38.
Sharbati-Tehrani et al., miR-Q: a novel quantitative RT-PCR approach for the expression profiling of small RNA molecules such as miRNAs in a complex sample, BMC Mol Biol, 2008, 9:34.
Shi et al., Facile means for quantifying microRNA expression by realtime PCR, Biotechniques, 2005, 39:519-525.
Tang et al., MicroRNA expression profiling of single whole embryonic stem cells, Nucleic Acids Res, 2006, 34:e9.
Too, Real time PCR quantification of GFRalp~~ha-2 alternatively spliced isoforms in murine brain and peripheral tissues, Res Mol Brain Res, 2003, 114:146-153.
Varkonyi-Gasic et al., Protocol: a highly sensitive RT-PCR method for detection and quantification of microRNAs, Plant Methods, 2007, 3:12.
Visone et al., MiRNAs and cancer. Am J Pathol. Apr. 2009;174(4):1131-8. Epub Mar. 5, 2009.
Wang et al., Direct and sensitive miRNA profiling from low-input total RNA, RNA, 2007, 13:151-159.
Wulczyn et al., Post-transcriptional regulation of the let-7 microRNA during neural cell specification, FASEB J, 2007, 21:415-426.
Yang et al., A novel real-time polymerase chain reaction method for high throughput quantification of small regulatory RNAs, Plant Biotechnol J, 2009, 7:621-630.
Yang et al., MicroRNA microarray identifies Let-7i as a novel biomarker and therapeutic target in human epithelial ovarian cancer, Cancer Res, 2008., 68:10307-10314.
Yao et al., Quantitative analysis of zeptomole microRNAs based on isothermal ramification amplification, RNA, 2009, 15:1787-1794.
Office Action, dated Apr. 16, 2015, in Chinese Application No. 201180038333.8.
Japanese Office Action, dated Jul. 6, 2015, in connection with Application No. 2013-515301.
European Office Action, dated May 30, 2016, in connection with European Application No. 11796068.2.

* cited by examiner

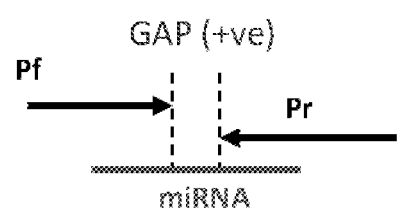
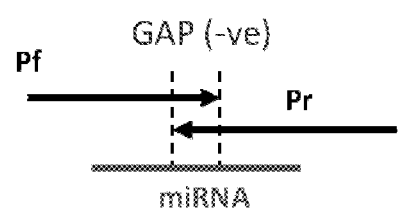
GAP
miR-21: -2
miR-24: +2
miR-92: -1
miR-218: -2
FIGURE 6

| Loop | Ct | | ΔCt |
|---|---|---|---|
| | Large (11/12nt) | Small (4nt) | (Ct $_{small\ loop}$ - Ct $_{large\ loop}$) |
| miR-21 | 30.2 | 29.1 | -1.0 |
| miR-218 | 22.4 | 22.3 | -0.2 |
| miR-24 | 22.4 | 22.1 | -0.3 |

FIGURE 7

A
let-7a UGAGGUAGUAGGUUGUAUAGUU
let-7b UGAGGUAGUAGGUUGUGUGGUU
let-7c UGAGGUAGUAGGUUGUAUGGUU
let-7f UGAGGUAGUAGAUUGUAUAGUU
let-7g UGAGGUAGUAGUUUGUACAGU-
let-7i UGAGGUAGUAGUUUGUGCUGU-
let-7d AGAGGUAGUAGGUUGCAUAGU-
let-7e UGAGGUAGGAGGUUGUAUAGU-

B

| Relative Detection (%) | | miRNA real-time RT-PCR assay | | | | | | | |
|---|---|---|---|---|---|---|---|---|---|
| | | let-7a | let-7b | let-7c | let-7d | let-7e | let-7f | let-7g | let-7i |
| Synthetic miRNA target | let-7a | 100.0 | 0.001 | 0.036 | 0.005 | 0.225 | 0.298 | 0.000 | 0.000 |
| | let-7b | 0.002 | 100.0 | 0.248 | 0.002 | 0.001 | 0.001 | 0.000 | 0.000 |
| | let-7c | 1.778 | 0.178 | 100.0 | 0.001 | 0.003 | 0.075 | 0.000 | 0.000 |
| | let-7d | 0.072 | 0.000 | 0.000 | 100.0 | 0.000 | 0.000 | 0.000 | 0.000 |
| | let-7e | 0.002 | 0.000 | 0.000 | 0.000 | 100.0 | 0.000 | 0.000 | 0.000 |
| | let-7f | 0.029 | 0.000 | 0.000 | 0.002 | 0.002 | 100.0 | 0.000 | 0.000 |
| | let-7g | 0.000 | 0.000 | 0.000 | 0.000 | 0.001 | 0.000 | 100.0 | 0.000 |
| | let-7i | 0.000 | 0.000 | 0.000 | 0.001 | 0.001 | 0.000 | 0.001 | 100.0 |

FIGURE 11

Table 1

| miRNA Assay | Mature (Stem-loop RT) | | | Mature (Linear RT) | | |
|---|---|---|---|---|---|---|
| miRNA Target | Precursor (Ct) | Mature (Ct) | ΔCt | Precursor (Ct) | Mature (Ct) | ΔCt |
| miR-21 | 28.0 | 18.9 | 9.1 | 28.5 | 27.6 | 0.9 |
| miR-7-1 | 30.2 | 18.1 | 14.1 | 32.9 | 22.5 | 10.4 |
| miR-7-2 | 26.0 | 18.1 | 9.9 | 26.7 | 22.5 | 4.2 |
| miR-218-1 | 28.7 | 15.8 | 12.9 | 24.1 | 16.6 | 7.6 |
| miR-218-2 | 25.0 | 15.8 | 9.2 | 25.8 | 16.6 | 9.2 |
| let-7f-1 | 21.6 | 18.2 | 3.4 | 20.4 | 20.8 | -0.4 |
| let-7f-2 | 26.8 | 18.2 | 8.6 | 26.9 | 20.8 | 6.1 |
| let-7g | 26.8 | 18.6 | 8.2 | 27.1 | 21.7 | 5.4 |
| let-7i | 21.7 | 18.6 | 3.1 | 20.9 | 20.9 | 0.0 |

FIGURE 21

Table 2

| | Primer Sequence | |
|---|---|---|
| miRNAs | Cloning (Forward) | Cloning (Reverse) |
| miR-7-1 | TAATACGACTCACTATAGGGTTGGATGTTG | CTGTAGAGGCATGGCCTGTGC |
| miR-7-2 | TAATACGACTCACTATAGGGCTGGATACAG | TGCGATGGCTGGCACCATTAG |
| miR-218-1 | TAATACGACTCACTATAGGGGTGATAATGTA | TGTAGAAAGCTGCGTGACGTTCC |
| miR-218-2 | TAATACGACTCACTATAGGGGACCAGTCGC | TGCAGGAGAGCACGGTGCTTTCCG |
| miR-21 | TAATACGACTCACTATAGGGTGTCGGGTAGC | TGTCAGACAGCCCATCGACT |
| let-7f-1 | TAATACGACTCACTATAGGGTCAGAGTGAG | TCAGGGAAGGCAATAGATTGTATAGTTATCTCC |
| let-7f-2 | TAATACGACTCACTATAGGGTGTGGGATGA | CGTGGGAAAGACAGTAGACTGTATAGTTATC |
| let-7g | TAATACGACTCACTATAGGGAGGCTGAGGT | TGGCAAGGCAGTGGCCTGTACAGTT |
| let-7i | TAATACGACTCACTATAGGGCTGGCTGAGG | TAGCAAGGCAGTAGCTTGCGCAGTTATCTC |

FIGURE 22

Table 3

| miRNAs | RT | PCR Forward | PCR Reverse |
|---|---|---|---|
| let-7a | GCTCAGACAGAAGTCACACTGAGCAACTAT | GGGCGGTGAGGTAGTAGG | GAAGTCACACTGAGCAACTATACAAC |
| let-7b | GCTCAGACAGAAGTCACACTGAGCAACAC | Same to let-7a | CACACTGAGCAACCACACAAC |
| let-7c | GCTCAGACAGAAGTCACACTGAGCAACCAT | Same to let-7a | TCACACTGAGCAACCATACAAC |
| let-7d | GCTCAGACAGAAGTCACACTGAGCACTATG | GCGGGCGGAGAGGTAGT | GTCACACTGAGCACTATGCAAC |
| let-7e | GCTCAGACAGAAGTCACACTGAGCACTATA | GGGCGGGTGAGGTAGG | AGAAGTCACACTGAGCACTATACAAC |
| let-7f | Same to let-7a | CGGGCGGTGAGGTAGTAGA | AGAAGTCACACTGAGCAACTATACAAT |
| let-7g | GCTCAGACAGAAGTCACACTGAGCACTGTA | CCGGGCGGTGAGGTAGTAGT | AAGTCACACTGAGCACTGTACAAA |
| let-7i | GCTCAGACAGAAGTCACACTGAGCACACGA | CCGGGCGGTGAGGTAGTAGT | CACACTGAGCACAGCACAAA |
| miR-24 | CACCGTTCCCCGCCGTCGGTGCTGTTC | GGGGCCTGGCTCAGTTC | CCGTCGGTGCTGTTCCTG |
| miR-92 | CACCGTTCCCCGCCGTCGGTGCAGGCC | CCCGCCTATTGCACTTGTC | GTCGGTGCAGGCCGGG |
| miR-18b | CACCGTTCCCCGCCGTCGGTGGACAAA | CCGCCGGTACCCTGTAGAA | CGTCGGTCCACAAATTGG |
| miR-221 | CACCGTTCCCCGCCGTCGGTGGAAACC | CGGGCAGCTACATTGTCTG | CGTCGGTGGAAACCAGCA |
| miR-222 | CACCGTTCCCCGCCGTCGGTGACCCAG | CGGGCAGCTACATCGG | CGTCGGTGACCCAGTAGC |
| miR-23 | CACCGTTCCCCGCCGTCGGTGTCAACA | CGGGCCTAGCTTATCAGACTG | GCCGTCGGTGTCAACATCA |
| miR-486-5p | CACCGTTCCCCGCCGTCGGTGCTCGGG | CGCCGTCCTGTACTGAGCT | GTCGGTGCTCGGGGCAG |
| miR-451 | CACGGAACCCCGCCGACCGTGAACTCA | CGGCGAAACCGTTACCAT | GCCGACCGTGAACTCAGTAAT |
| miR-15b | CACCGTTCCCCGCCGTCGGTGTGTAAA | CCGCCGTAGCAGCACATC | CCGTCGGTGTGTAAACCATG |
| miR-146b-5p | CACCGTTCCCCGCCGTCGGTGGAGCCTA | CGGGCGGTGAGAACTGAATT | CGTCGGTGAGCCTATGGA |
| miR-128 | CACGGAACCCCGCCGACCGTGAAAGAG | GGCCGTCACACTGAACCG | CGACCGTGAAAGAGACCG |
| miR-181c | CACGGAACCCCGCCGACCGTGACTCAC | CCGCCGAACATTCAACCT | CGACCGTGACTCACCGAC |
| miR-181a | Same to miR-181c | CGCCGAACATTCAACGC | Same to miR-181c |
| miR-181b | CACGGAACCCCGCCGACCGTGACCCAC | CCGCCGAACATTCATTGC | GACCGTGACCCACGGAC |
| miR-426 | CACCGTTCCCCGCCGTCGGTGTCTCAACG | GGGCGAATGACACGGATCAC | CGTCGGTGTCTCAACGGGAG |
| miR-7 | CACCGTTCCCCGCCGTCGGTGACAACA | CGCCCTGGAAGACTAGTGAT | CGGTCGGTGACAACAAAAT |
| miR-124 | CACCGTTCCGGCGCCGTGGGTGGCATT | CATACCTAAGGCACGCGG | GTCGGTCGGGCATTCACC |
| miR-137 | CACCGTTCCCCGCCGTCGGTGCTACGC | CCGGCCGTTATTGCTTAAGAA | CGTCGGTGCTACGCGTAT |
| miR-139-5p | CACCGTTCCCCGCCGTCGGTGCTGGAG | GCGGCCTCTACAGTGCACGT | CGTCGGTGCTGGAGACAC |
| miR-218 | CACCGTTCCCCGCCGTCGGTGACATGG | TCGGGCTTGTGCTTGATCT | CCGTCGGTGACATGGTTAG |

FIGURE 23

Table 4

| miRNA | RT Oligonucleotide | Sequence | Tm (°C) | ΔG$_{RT}$ (kcal/mol) | ΔG$_{PCR}$ (kcal/mol) |
|---|---|---|---|---|---|
| miR-21 | Stem-loop | CACCGTTCGCGGCCGTCGGTGTCAACA | 86.2 | -2.37 | 0.19 |
| | Linear | GACCGTTCGCGGCCGTCGGTGTCAACA | 85.6 | -0.18 | 1.21 |
| miR-7 | Stem-loop | CACCGTTCGCGGCCGTCGGTGACAACA | 86.2 | -2.98 | -0.55 |
| | Linear | GACCGTTCGCGGCCGTCGGTGACAACA | 85.6 | -0.18 | 1.21 |
| miR-218 | Stem-loop | CACCGTTCGCGGCCGTCGGTGACATGG | 87.1 | -2.98 | -0.55 |
| | Linear | GACCGTTCGCGGCCGTCGGTGACATGG | 86.4 | -0.18 | 1.21 |
| let-7f | Stem-loop | GCTCAGACAGAAGTCACATTGAGCAACTAT | 71.0 | -3.22 | -0.20 |
| | Linear | CGAGAGTCAGAAGTCACATTGAGCAACTAT | 70.9 | -0.02 | 1.40 |
| let-7g | Stem-loop | GCTCAGACAGAAGTCACACTGAGCACTGTA | 72.8 | -3.22 | -0.20 |
| | Linear | CGAGAGTCAGAAGTCACACTGAGCACTGTA | 72.8 | -0.02 | 1.40 |
| let-7i | Stem-loop | GCTCAGACAGAAGTCACACTGAGCACAGCA | 77.2 | -3.22 | -0.20 |
| | Linear | CGAGAGTCAGAAGTCACACTGAGCACAGCA | 77.2 | -0.58 | 1.17 |

FIGURE 24

Table 5

| SEQUENCE | SEQ ID NO |
|---|---|
| TAATACGACTCACTATAGGGTTGGATGTTG | 1 |
| CTGTAGAGGCATGGCCTGTGC | 2 |
| TAATACGACTCACTATAGGGCTGGATACAG | 3 |
| TGCGATGGCTGGCACCATTAG | 4 |
| TAATACGACTCACTATAGGGTGATAATGTA | 5 |
| TGTAGAAAGCTGCGTGACGTTCC | 6 |
| TAATACGACTCACTATAGGGGACCAGTCGC | 7 |
| TGCAGGAGAGCACGGTGCTTTCCG | 8 |
| TAATACGACTCACTATAGGTGTCGGGTAGC | 9 |
| TGTCAGACAGCCCATCGACT | 10 |
| TAATACGACTCACTATAGGGTCAGAGTGAG | 11 |
| TCAGGGAAGGCAATAGATTGTATAGTTATCTCC | 12 |
| TAATACGACTCACTATAGGGTGTGGGATGA | 13 |
| CGTGGGAAAGACAGTAGACTGTATAGTTATC | 14 |
| TAATACGACTCACTATAGGGAGGCTGAGGT | 15 |
| TGGCAAGGCAGTGGCCTGTACAGTT | 16 |
| TAATACGACTCACTATAGGGCTGGCTGAGG | 17 |
| TAGCAAGGCAGTAGCTTGCGCAGTTATCTC | 18 |
| GCTCAGACAGAAGTCACACTGAGCAACTAT | 19 |
| GGGCGGTGAGGTAGTAGG | 20 |
| GAAGTCACACTGAGCAACTATACAAC | 21 |
| GCTCAGACAGAAGTCACACTGAGCAACCAC | 22 |
| CACACTGAGCAACCACACAAC | 23 |
| GCTCAGACAGAAGTCACACTGAGCAACCAT | 24 |
| TCACACTGAGCAACCATACAAC | 25 |
| GCTCAGACAGAAGTCACACTGAGCACTATG | 26 |
| GCGGGCGGAGAGGTAGT | 27 |
| GTCACACTGAGCACTATGCAAC | 28 |
| GCTCAGACAGAAGTCACACTGAGCACTATA | 29 |
| CGGGCGGTGAGGTAGG | 30 |
| AGAAGTCACACTGAGCACTATACAAC | 31 |
| CGGGCGGTGAGGTAGTAGA | 32 |
| AGAAGTCACACTGAGCAACTATACAAT | 33 |
| GCTCAGACAGAAGTCACACTGAGCACTGTA | 34 |

FIGURE 25

Table 5 (Continued)

| SEQUENCE | SEQ ID NO |
|---|---|
| CGGGCGGTGAGGTAGTAGT | 35 |
| AAGTCACACTGAGCACTGTACAAA | 36 |
| GCTCAGACAGAAGTCACACTGAGCACAGCA | 37 |
| CGGGCGGTGAGGTAGTAGT | 38 |
| CACACTGAGCACAGCACAAA | 39 |
| CACCGTTCCCCGCCGTCGGTGCTGTTC | 40 |
| CCCGCCTGGCTCAGTTC | 41 |
| CCGTCGGTGCTGTTCCTG | 42 |
| CACCGTTCCCCGCCGTCGGTGCAGGCC | 43 |
| CCCGCCTATTGCACTTGTC | 44 |
| GTCGGTGCAGGCCGGG | 45 |
| GACCGTTCCCCGCCGTCGGTCCACAAA | 46 |
| CCGCCGTACCCTGTAGAA | 47 |
| CGTCGGTCCACAAATTCG | 48 |
| CACCGTTCCCCGCCGTCGGTGGAAACC | 49 |
| CGGGCAGCTACATTGTCTG | 50 |
| CGTCGGTGGAAACCAGCA | 51 |
| CACCGTTCCCCGCCGTCGGTGACCCAG | 52 |
| CGGGCAGCTACATCTGG | 53 |
| CGTCGGTGACCCAGTAGC | 54 |
| CACCGTTCCCCGCCGTCGGTGTCAACA | 55 |
| CCCGCCTAGCTTATCAGACTG | 56 |
| GCCGTCGGTGTCAACATCA | 57 |
| CACCGTTCCGCGCCGTCGGTGCTCGGG | 58 |
| CGCCGTCCTGTACTGAGCT | 59 |
| GTCGGTGCTCGGGGCAG | 60 |
| CACGGAACCCCGCCGACCGTGAACTCA | 61 |
| CGCCGAAACCGTTACCAT | 62 |
| GCCGACCGTGAACTCAGTAAT | 63 |
| CACCGTTCCCCGCCGTCGGTGTGTAAA | 64 |
| CCGCCGTAGCAGCACATC | 65 |
| CCGTCGGTGTGTAAACCATG | 66 |
| CACCGTTCCCCGCCGTCGGTGAGCCTA | 67 |
| CGGGCGTGAGAACTGAATT | 68 |

FIGURE 25 (continued)

Table 5 (Continued)

| SEQUENCE | SEQ ID NO |
|---|---|
| CGTCGGTGAGCCTATGGA | 69 |
| CACGGAACCCCGCCGACCGTGAAAGAG | 70 |
| GGCGTCACAGTGAACCG | 71 |
| CGACCGTGAAAGAGACCG | 72 |
| CACGGAACCCCGCCGACCGTGACTCAC | 73 |
| CCGCCGAACATTCAACCT | 74 |
| CGACCGTGACTCACCGAC | 75 |
| CGCCGAACATTCAACGC | 76 |
| CACGGAACCCCGCCGACCGTGACCCAC | 77 |
| CCGCCGAACATTCATTGC | 78 |
| GACCGTGACCCACCGAC | 79 |
| GACCGTTCCCCGCCGTCGGTCTCAACG | 80 |
| GGGCGAATGACACGATCAC | 81 |
| CGTCGGTCTCAACGGGAG | 82 |
| CACCGTTCCCCGCCGTCGGTGACAACA | 83 |
| CGCCCTGGAAGACTAGTGAT | 84 |
| CCGTCGGTGACAACAAAAT | 85 |
| CACCGTTCCGCGCCGTCGGTGGGCATT | 86 |
| CATACCTAAGGCACGCGG | 87 |
| GTCGGTGGGCATTCACC | 88 |
| CACCGTTCCCCGCCGTCGGTGCTACGC | 89 |
| CCGCCGTTATTGCTTAAGAA | 90 |
| CGTCGGTGCTACGCGTAT | 91 |
| CACCGTTCCCCGCCGTCGGTGCTGGAG | 92 |
| CCGCCTCTACAGTGCACGT | 93 |
| CGTCGGTGCTGGAGACAC | 94 |
| CACCGTTCCCCGCCGTCGGTGACATGG | 95 |
| TCGGGCTTGTGCTTGATCT | 96 |
| CCGTCGGTGACATGGTTAG | 97 |
| CACCGTTCCCCGCCGTCGGTGTCAACA | 98 |
| GACCCTTCGCGGCCGTCGGTGTCAACA | 99 |
| CACCGTTCCCCGCCGTCGGTGACAACA | 100 |
| GACCCTTCGCGGCCGTCGGTGACAACA | 101 |
| CACCGTTCCCCGCCGTCGGTGACATGG | 102 |

FIGURE 25 (continued)

Table 5 (Continued)

| SEQUENCE | SEQ ID NO |
|---|---|
| GACCCTTCGCGGCCGTCGGTGACATGG | 103 |
| GCTCAGACAGAAGTCACACTGAGCAACTAT | 104 |
| CGAGAGTCAGAAGTCACACTGAGCAACTAT | 105 |
| GCTCAGACAGAAGTCACACTGAGCACTGTA | 106 |
| CGAGAGTCAGAAGTCACACTGAGCACTGTA | 107 |
| GCTCAGACAGAAGTCACACTGAGCACAGCA | 108 |
| CGAGAGTCAGAAGTCACACTGAGCACAGCA | 109 |
| UAGCUUAUCAGACUGAUGUUGA | 110 |
| TCAACATCAGTCTGATAAGCTA | 111 |
| TAGCTTATCAGACTGATGTTGA | 112 |
| CACCGTTCCCCGCCGTCGGTGTCAACA | 113 |
| CCCGCCTAGCTTATCAGACTG | 114 |
| GCCGTCGGTGTCAACATCA | 115 |
| UGAGGUAGUAGGUUGUAUAGUU | 116 |
| UGAGGUAGUAGGUUGUGUGGUU | 117 |
| UGAGGUAGUAGGUUGUAUGGUU | 118 |
| UGAGGUAGUAGAUUGUAUAGUU | 119 |
| UGAGGUAGUAGUUUGUACAGU | 120 |
| UGAGGUAGUAGUUUGUGCUGU | 121 |
| AGAGGUAGUAGGUUGCAUAGU | 122 |
| UGAGGUAGGAGGUUGUAUAGU | 123 |
| GCTCAGACAGAAGTCACACTGAGCAACTAT | 124 |
| GCTCAGACAGAAGUCACACTGAGCAACTAT | 125 |
| GCTCAGACAGAAGTCACACUGAGCAACTAT | 126 |
| CACCGTTTTCTTTCGGTGTCAACA | 127 |
| CACCGUUUUCUUUCGGTGTCAACA | 128 |

FIGURE 25 (continued)

MODIFIED STEM-LOOP OLIGONUCLEOTIDE MEDIATED REVERSE TRANSCRIPTION AND BASE-SPACING CONSTRAINED QUANTITATIVE PCR

CROSS-REFERENCE TO RELATED APPLICATION

The present application is a national stage filing under 35 U.S.C. §371 of international PCT application, PCT/SG2011/000210, filed Jun. 13, 2011, which claims priority under 35 U.S.C. §119(e) to U.S. provisional patent application, U.S. Ser. No. 61/354,683, filed on Jun. 14, 2010; each of which is incorporated herein by reference.

FIELD OF THE INVENTION

The invention relates to methods of detecting a target RNA in a sample, including detecting a target miRNA in a sample.

BACKGROUND OF THE INVENTION

MicroRNAs (miRNAs) are small non-coding RNAs (typically about 22 nucleotides in length) that were discovered as important post-transcriptional regulators of gene expression in metazoans (Bartel, 2004). While expression of miRNAs are critical in various physiological processes (Harfe, 2005; Miska, 2005; Carthew, 2006; Lindsay, 2008), dysregulation of miRNAs are implicated in pathologies of many human diseases such as cancer (Visone & Croce, 2009), muscle disorders (Chen et al., 2009a) and neurodegeneration (Hebert & De Strooper, 2009).

Recently, mature miRNAs were found to be remarkably stable in blood, and thus hold great promise as potential noninvasive biomarkers of human diseases (Chen et al., 2008; Mitchell et al., 2008). To date, hundreds of unique miRNAs have been identified in many species and each of these is predicted to regulate diverse target genes (Bartel, 2009). With the continual discovery of more miRNAs by both in silico prediction and in vivo validation (Mendes et al., 2009), profiling of miRNA expression remains an essential tool not only for assessment of distribution and regulation of miRNAs but also for identification of novel biomarkers and potential therapeutic targets.

Mature miRNAs can be detected by either direct or indirect methods. Although direct detection methods (eg. fluorescent, colorimetric and electrical-based methods) can minimize variations introduced during sample measurements, these methods are limited by low assay sensitivity and poor discrimination among miRNA homologs (reviewed in Hunt et al., 2009).

Indirect detection methods include primarily Northern blotting, microarray and reverse transcription PCR (RT-PCR). Although widely used, both Northern blotting and microarray are semi-quantitative and suffer from poor sensitivity and require large amounts of starting RNA. Although microarrays offer high-throughput detection of miRNAs and the potential capability of absolute quantification (Bissels et al., 2009), a recent study showed that real-time PCR remains superior in sensitivity and specificity in comparison (Chen et al., 2009b). Recent attempts to measure miRNA with isothermal methods have met with some success but are labor intensive (Cheng et al., 2009; Yao et al., 2009).

To date, real-time RT-PCR remains the most sensitive and efficient method for quantification of RNA species. TaqMan probe-based real-time RT-PCR has been reported and widely used for efficient and specific detection of miRNAs. However, due to an additional probe hydrolysis step, TaqMan assays were not compatible with fast thermo-cycling protocols for rapid detection of miRNAs. Furthermore, with the escalating identification of hundreds of candidate miRNAs by deep sequencing (Bar et al., 2008; Goff et al., 2009), design of TaqMan probe for each of the novel miRNA is not only cost-prohibitive but also technically challenging and faces practical difficulties (Varkonyi-Gasic et al., 2007).

Attempts have been made to improve miRNA detection without reliance on fluorescent probes (Raymond et al., 2005; Shi & Chiang, 2005; Sharbati-Tehrani et al., 2008), however, these assays usually involved multiple sample processing steps (Shi & Chiang, 2005) and suffered from limited dynamic range of detection (Raymond et al., 2005) and/or poor specificity against homologous miRNAs (Raymond et al., 2005; Shi & Chiang, 2005; Sharbati-Tehrani et al., 2008). A common strategy of these assays and some other TaqMan assays (Varkonyi-Gasic et al., 2007; Yang et al., 2009) is to use universal or common reverse PCR primer and/or fluorescent probe for amplification and detection of multiple miRNAs. In such assays, specificity of real-time PCR is only achieved by the forward PCR primer, which is not sufficient for discrimination of many homologous miRNAs. Furthermore, it is yet to be determined whether these assays are capable of rapid, multiplexed and direct detection of miRNAs without RNA isolation.

While the number of microRNAs in various genomes are still being identified, the number of different miRNA is expected to be as many as a few thousand. Since the Nobel prize was awarded in 2006 for RNA interference (A. Z. Fire & Craig C. Mello), the demand for assays to detect miRNA has steadily increased.

Thus, there exists a need for alternative methods of detecting a target RNA in a sample, including an miRNA.

SUMMARY OF THE INVENTION

The invention provides a method of detecting a target RNA molecule in a sample. The target RNA molecule may be any RNA molecule, and may be an miRNA in some embodiments.

The methods of the present invention use a combination of reverse transcription (RT) and polymerase chain reaction (PCR) amplification to specifically identify a target RNA from a sample containing the target RNA. The methods use a combination of a modified stem-loop RT oligonucleotide and hemi-nested PCR primers to specifically select for the target RNA. Use of a modified nucleotide within the RT oligonucleotide provides a block for DNA polymerase to prevent mis-priming during the amplification reaction. Thus, carry-over of the RT oligonucleotide to the amplification reaction may be reduced or even eliminated, while the specificity for a target miRNA may be enhanced even with the presence of miRNA homologs in the sample.

The methods of the invention may provide specific and rapid detection of target RNA species, such as mature miRNAs from precursor miRNAs and from homologous family members. It may be possible to use a fast thermo-cycling profile (10 seconds per cycle) yet still retain specificity and sensitivity.

The methods may also be used in multiplex format, which may be useful for screening and detection of miRNAs directly from cell lysates without the requirement for laborious total RNA isolation.

The methods of the invention may be tailored to existing real-time PCR methods. Real-time PCR has become the standard method for gene expression measurements and has become an extremely useful technique for gene profiling and for biomarker discovery.

The methods may be economical, high-performance, easy to use, rapid and sensitive.

Thus, in one aspect, the present invention provides a method for detecting a target RNA molecule in a sample, the method comprising: reverse transcribing the target RNA contained in the sample using an RT oligonucleotide, the RT oligonucleotide comprising a stem-loop portion containing one or more nucleotides modified or modifiable to block DNA polymerase extension and a target annealing portion that is complementary to a downstream portion of the target RNA, the target annealing portion located 3' to the stem-loop portion, to produce a reverse transcription product that comprises the RT oligonucleotide and a 3' extended region; amplifying the reverse transcription product using (i) a first amplification primer that anneals to a downstream portion of the 3' extended region of the reverse transcription product and (ii) a second amplification primer that anneals to an interface portion of a DNA strand complementary to the reverse transcription product, the interface portion comprising a region that is complementary to a 3' portion of the RT oligonucleotide and a 5' portion of the 3' extended region in the reverse transcription product, to produce an amplification product; and detecting the amplification product; wherein the stem-loop portion adopts a stem-loop structure under conditions used for said reverse transcribing but does not adopt the stem-loop structure under conditions used for said amplifying and wherein when the stem-loop portion contains one or more nucleotides that are modifiable to block DNA polymerase extension, the method further comprises modifying the modifiable nucleotide prior to said amplifying.

In some embodiments, the one or more nucleotides modified or modifiable to block DNA polymerase extension is located within the loop of the stem-loop portion.

In some embodiments, the stem-loop portion contains one or more nucleotides modified to block DNA polymerase extension. For example, the loop of the stem-loop portion may comprise a nucleotide modified with an aliphatic carbon chain, for example a C6 aliphatic chain.

Alternatively, in some embodiments the stem-loop portion contains one or more nucleotide modifiable to block DNA polymerase extension and the method further comprises modifying the modifiable nucleotide prior to the amplifying. For example, the modifiable nucleotide may be dU and the modifying may comprise treatment with uracil-DNA glycosylase. In another example, the loop of the stem-loop portion may comprise one or more ribonucleotides and the modifying may comprise treatment with RNAse.

In some embodiments, the target RNA is an miRNA.

In another aspect, the invention provides a method for detecting a target miRNA molecule in a sample, the method comprising: reverse transcribing the target miRNA contained in the sample using an RT oligonucleotide, the RT oligonucleotide comprising a stem-loop portion containing a dU nucleotide and a target annealing portion that is complementary to a downstream portion of the target miRNA, the target annealing portion located 3' to the stem-loop portion, to produce a reverse transcription product that comprises the RT oligonucleotide and a 3' extended region; modifying the dU nucleotide by treatment with uracil-DNA glycosylase; amplifying the reverse transcription product using (i) a first amplification primer that anneals to a downstream portion of the 3' extended region of the reverse transcription product and (ii) a second amplification primer that anneals to an interface portion of a DNA strand complementary to the reverse transcription product, the interface portion comprising a region that is complementary to a 3' portion of the RT oligonucleotide and a 5' portion of the 3' extended region in the reverse transcription product, to produce an amplification product; and detecting the amplification product; wherein the stem-loop portion adopts a stem-loop structure under conditions used for said reverse transcribing but does not adopt the stem-loop structure under conditions used for said amplifying.

In some embodiments of methods of the invention, the amplification primers have nucleotides that display thermal stability when hybridized to DNA as the 3' terminal nucleotide. For example, the nucleotide that displays thermal stability when hybridized to DNA may be locked in an N-type furanose conformation.

In some embodiments, including where the RNA is an miRNA, the distance in the sequence of the amplification product between the position of the 3' end of the first amplification primer when annealed to the reverse transcription product and the position of the 3' end of the second amplification primer when annealed to the DNA strand is from −4 to 5 nucleotides.

In some embodiments the target annealing portion of the RT oligonucleotide is 5 to 15 nucleotides in length.

In some embodiments the stem portion of the stem-loop is 4 to 6 nucleotides in length and the loop portion of the stem-loop is 4 to 12 nucleotides in length.

In some embodiments the second amplification primer anneals to a sequence complementary to 13 to 24 nucleotides of the stem-loop portion of the RT oligonucleotide, 5 to 15 nucleotides of the target annealing portion of the RT oligonucleotide and 1 to 5 nucleotides at the 5' end of the 3' extended region of the reverse transcription product.

In some embodiments the first amplification primer is 12 to 27 nucleotides in length.

In some embodiments the detecting comprises detecting with a fluorescent intercalating dye. For example, the fluorescent intercalating dye may be SYBR GREEN™.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The tables and figures, which illustrate, by way of example only, embodiments of the present invention, are as follows.

FIG. 6. Placement of first amplification (Pf) and second amplification (Pr) primers, showing gap or overlap.

FIG. 7. Comparison of size of loop. Small loops (4 bases) perform comparably to larger loops (12 bases).

FIG. 11. Discrimination of human let-7 homologs. A) Sequence alignment of the eight let-7 family miRNAs. B) Relative detection (%) of each let-7 miRNA by specific hemi-nested real-time RT-PCR assays. The primer sequences shown correspond to SEQ ID NOs. 116-123 as shown in FIG. 25 (Table 5).

FIG. 21 (Table 1). Discrimination between mature and precursor miRNAs using stem-loop or linear real-time RT-PCR. $10^9$ copies of each synthetic mature miRNAs or in vitro transcribed pre-miRNAs were reverse transcribed with either stem-loop or linear RT oligonucleotide and quantified using the same PCR primers. Discrimination between mature and precursor miRNAs was expressed as ΔCt values ($\Delta Ct = Ct_{Precursor} - Ct_{Mature}$).

FIG. 22 (Table 2). Primer sequences for cloning and real-time RT-PCR of miRNA precursors. The sequences shown in Table 2 correspond to SEQ ID NOs. 1-18 in FIG. 25 (Table 5).

FIG. 23 (Table 3). Primer sequences for detection of mature miRNAs. The sequences shown in Table 3 correspond to SEQ ID NOs. 19-97 in FIG. 25 (Table 5).

FIG. 24 (Table 4). Comparison of stem-loop and linear RT oligonucleotides. The most stable secondary structure was adopted to calculate ΔG for linear RT oligonucleotides. Sequence differences between stem-loop and linear RT oligonucleotides for each miRNA are underlined. The sequences shown in Table 2 correspond to SEQ ID NOs. 98-109 in FIG. 25 (Table 5).

FIG. 25 (Table 5) lists the various sequences set out in the Figures, assigning a SEQ ID NO for each sequence.

DETAILED DESCRIPTION

There is presently provided a method for detection of RNA from a sample. The method may be used to detect any RNA species, and may be useful in detecting mature miRNA, including directly from a cell containing the miRNA.

The method is an RT-PCR (reverse transcription-PCR) amplification method that combines an RT oligonucleotide primer designed to have stem-loop secondary structure and a nucleotide modified to block DNA polymerase during an amplification reaction together with a pair hemi-nested amplification primers in the amplification reaction.

Figure 1:
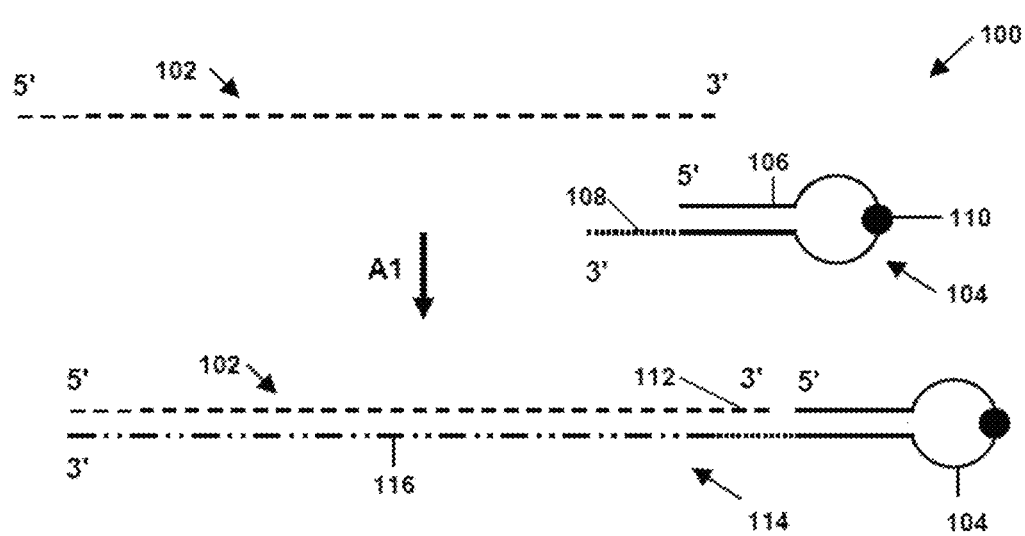
FIG. 1 is a schematic representation that provides an overview of the reverse transcription stage of the method of the invention.
Figure 2:
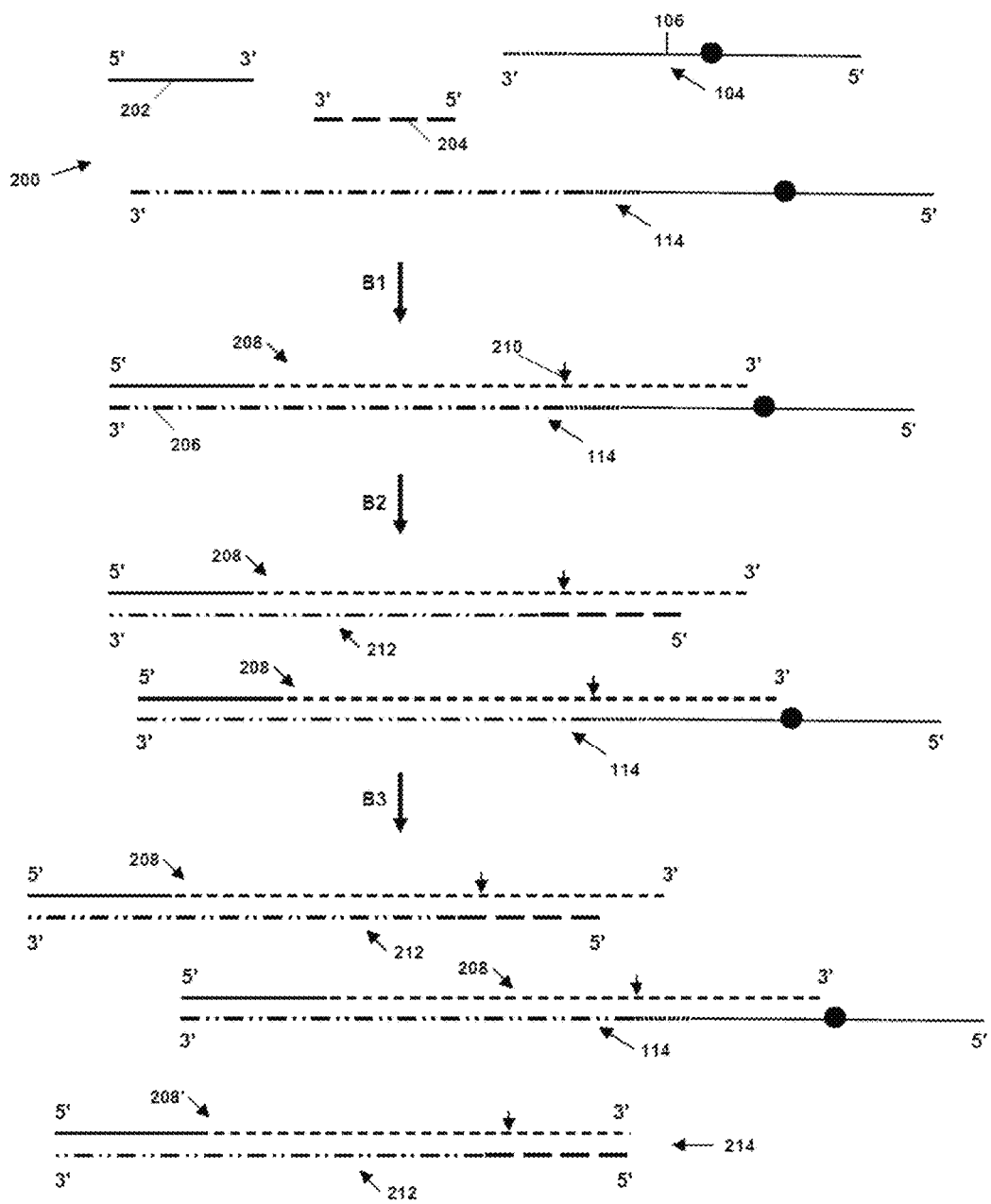
FIG. 2 is a schematic representation that provides an overview of the amplification stage of the method of the invention.

FIGS. 1 and 2 provide a schematic representation of an overview of the method; the 5' and 3' end of each nucleic acid molecule depicted is indicated. FIG. 1 represents a reverse transcription reaction and FIG. 2 represents an amplification reaction.

In the reverse transcription stage (FIG. 1) of the method, the initial reaction mixture 100 contains the target RNA 102 that is to be reverse transcribed, and a reverse transcription (RT) oligonucleotide 104 that acts as a primer for the reverse transcription reaction. RT oligonucleotide 104 has stem-loop portion 106 and target annealing portion 108. Under the conditions used in the reverse transcription reaction, for example a reaction temperature of about 37° C., the stem-loop portion 106 is in an annealed conformation having a stem-loop structure, as depicted in FIG. 1. The stem-loop portion 106 contains one or more nucleotides 110 modified or modifiable to block DNA polymerase extension.

In the reverse transcription reaction A1, the target annealing portion 108 anneals to a downstream portion 112 of target RNA 102 and is then extended by a reverse transcriptase enzyme to produce a reverse transcription product 114 that comprises RT oligonucleotide 104 and a 3' extended region 116.

In the amplification stage (FIG. 2) of the method, the initial reaction mixture 200 contains the reverse transcription product 114, a first amplification primer 202 and a second amplification primer 204. In addition, the initial reaction mixture 200 may also contain some RT oligonucleotide 104 carried over from the reverse transcription reaction, which may thus also act as a primer. Under the conditions used in the amplification reaction, for example a reaction temperature of about 50° C. or higher, the stem-loop portion 106 is in a melted conformation that does not have a stem-loop structure, as depicted in FIG. 2.

In the first round of amplification B1, the reverse transcription product 114 acts as a template and the first amplification primer 202 binds to a downstream portion 206 of reverse transcription product 114. A DNA polymerase enzyme extends first amplification primer 202 until nucleotide 110 is reached, blocking further extension, thus producing a complementary DNA strand 208 that is complementary to the reverse transcription product and that has a 3' end in the vicinity of the complementary position to nucleotide 110. Complementary DNA strand 208 has an interface portion 210 that comprises a region that is complementary to interface in reverse transcription product 114 formed by the interface between the 3' end of RT oligonucleotide 104 and the 5' end of 3' extended region 116.

In the second round of amplification B2, second amplification primer 204 anneals to complementary DNA strand 208 at interface portion 210, and complementary DNA strand 208 acts as a template for DNA polymerase extension to produce DNA strand 212. Since second amplification primer 204 is thus nested in from the end of complementary strand 208, DNA strand 212 has a portion of the sequence of reverse transcription product 114, but is shorter than reverse transcription product 114.

In subsequent rounds of amplification B3, first amplification primer 202 and second amplification primer 204 will anneal to available DNA template strands. When first amplification primer 202 anneals to DNA strand 212, the complementary DNA strand 208' that is formed is shorter than complementary DNA strand 208. DNA strand 212 and complementary DNA strand 208' thus form amplification product 214. Although some longer DNA strands such as reverse transcription product 114 and complementary DNA strand 208 will be present to serve as template, as the amplification reaction progresses through multiple rounds, more amplification product 214 is produced, due to the inclusion of nucleotide 110 and due to the nesting of second amplification primer 204.

Figure 3:
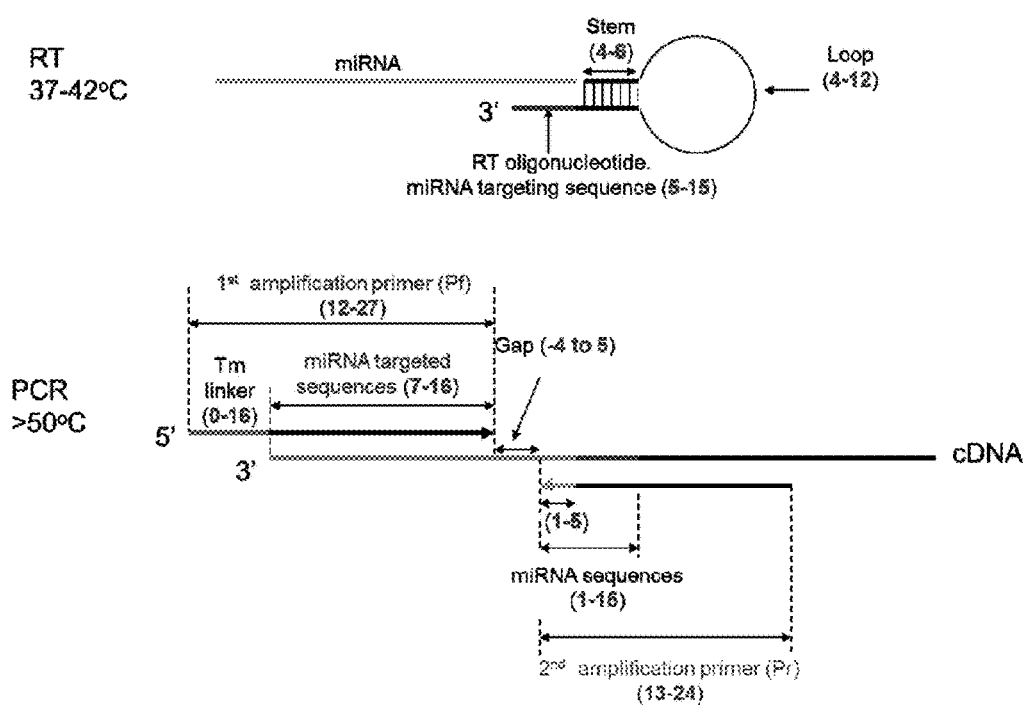
FIG. 3. Schematic diagram providing overview of an embodiment of the method of the invention.
Figure 4:
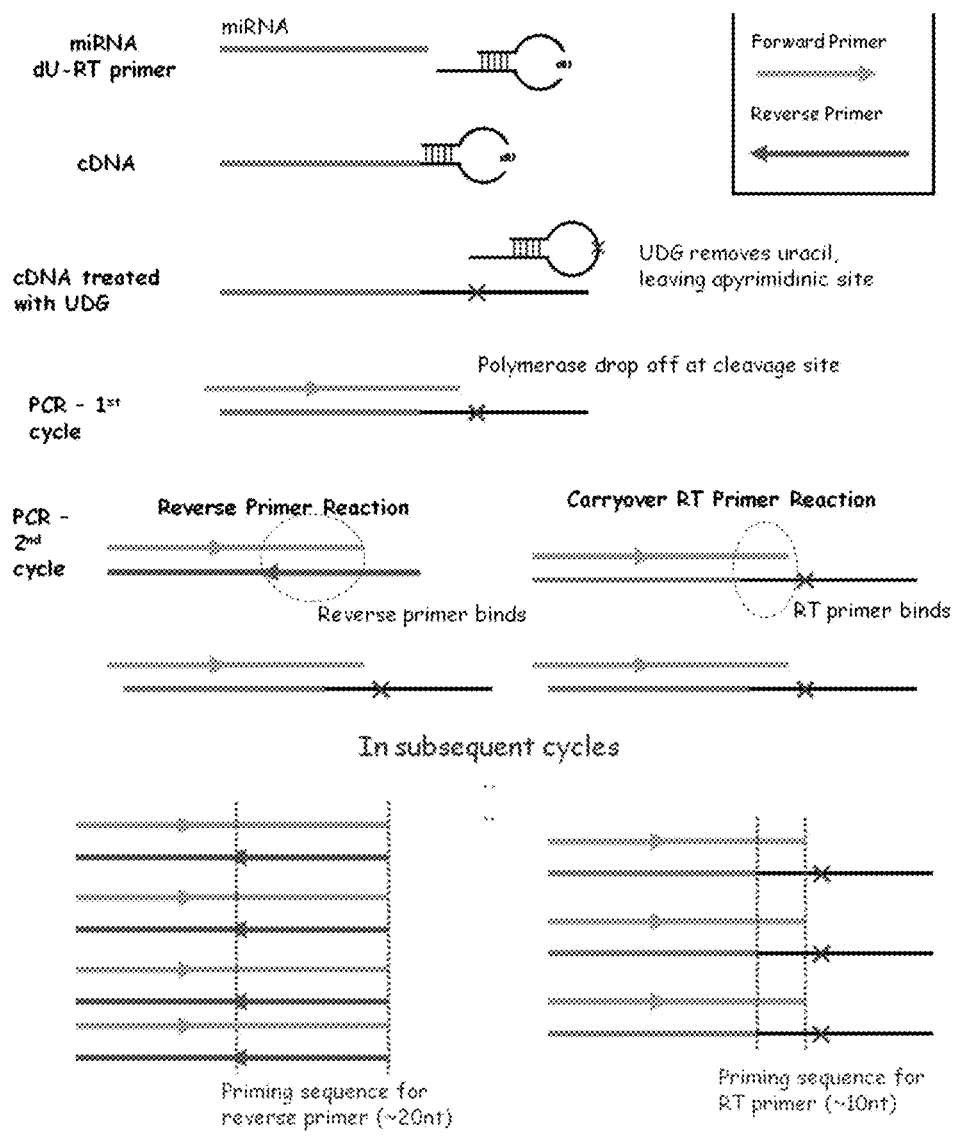
FIG. 4. DNA block (dU) inhibits DNA extension by DNA polymerase.

A further schematic depiction of the method is provided in FIG. 3. FIG. 4 depicts the effect of the modified nucleotide to block DNA polymerase on the specificity of the amplification reaction.

In a number of previous reports (Chen et al., 2005; Raymond et al., 2005; Shi & Chiang, 2005; Duncan et al., 2006; Varkonyi-Gasic et al., 2007; Sharbati-Tehrani et al., 2008; Yang et al., 2009), reverse amplification primers were designed to anneal directly to sequences in the RT oligonucleotide. To achieve specificity in such methods, a unique miRNA-specific fluorescent probe is required to discriminate the targets from nonspecific amplicons (Chen et al., 2005). In the case of some TaqMan-based assays, this specificity was compromised for the convenience of throughput by using one common probe for detection. In contrast, in the method as described herein, increased specificity can be achieved by designing a hemi-nested reverse PCR primer that is designed to anneal to part of the reverse transcription oligonucleotide primer and part of the 3' extended region the product of reverse transcription.

In contrast to quantitative real-time PCR methods, the method described herein does not require the use of a fluorescent probe, as the hemi-nested reverse amplification primer enhances the assay specificity, and may allow quantification of as little as subzeptomole amounts of miRNA using a fluorescent intercalating dye such as SYBR GREEN™ I under rapid thermo-cycling conditions.

Thus, in one aspect there is provided a method for detecting target RNA in a sample.

The method comprises a reverse transcription reaction. A reverse transcription reaction is performed on a sample that contains the target RNA, using an RT oligonucleotide as a primer for the reaction.

As will be appreciated, the RT oligonucleotide thus acts as primer for a reverse transcriptase enzyme that uses the target RNA as a template and extends the RT oligonucleotide to form a reverse transcription product that comprises the RT oligonucleotide at the 5' end and an extended region at the 3' end of the reverse transcription product.

The RT oligonucleotide comprises a stem-loop portion and a target annealing portion located 3' to the stem-loop portion.

Thus, the RT oligonucleotide used in the reverse transcription reaction is a DNA oligonucleotide that is designed to have a 5' portion that contains a stem-loop structure. As will be understood, the stem-loop structure is a self-annealing structure that has complementary base sequences that pair together to form a short duplex DNA stem. The loop is formed by nucleotides that intervene between the two complementary regions that form the stem and forms a single stranded section at one end of the stem, connecting the two portions that form the double stranded stem.

The stem-loop portion is designed to adopt the stem-loop structure under conditions used for the reverse transcription reaction, meaning under the conditions including the buffer, salt and temperature conditions and any other parameter that would affect DNA secondary structure, which are chosen to permit the reverse transcriptase enzyme used in the reaction conduct the reverse transcription. The stem-loop portion is also designed to melt, or to not adopt the stem-loop structure under the conditions used for the amplification reaction as discussed below. Thus, the sequence of the stem portion may be selected to anneal at the temperature used for reverse transcription, including taking into consideration the relevant buffer conditions, but not to anneal at the temperature used for amplification reaction, again including taking into consideration the relevant buffer conditions. For example, the stem-loop portion may adopt the stem-loop structure at 37° C. or lower, but may not anneal to form the stem-loop structure at about 50° C. or higher.

The stem-loop portion of the RT oligonucleotide includes a DNA polymerase blocking position. The DNA polymerase blocking position is a position in the stem-loop region that, when linearised and not adopting the stem-loop structure, acts as a block for an elongating DNA polymerase that is extended an amplification primer in the amplification reaction, using the reverse transcription product as a template.

The DNA blocking position may be positioned anywhere within the stem-loop portion of the RT oligonucleotide. In one embodiment, the DNA blocking position is positioned within the loop of the stem-loop portion.

The DNA blocking position can be any modification to the stem-loop region that blocks primer extension by the elongating DNA polymerase. For example, the DNA blocking position may be a modified nucleotide that cannot be read by the DNA polymerase, for example using a derivative of a DNA nucleotide or a modified DNA nucleotide having an attached chemical group.

The modification may be an altered structure of the nucleic base of the modified nucleotide; that is it may be an analog of A, G, C or T which DNA polymerase cannot use as a template or extend past.

The modification may be a group that is a substituent on a nucleotide at the DNA blocking position, including a non-nucleotide group, and may be a pendant group or may be attached to two nucleotides so that the group forms part of the oligonucleotide backbone. For example, the DNA blocking position may be in the loop region and may include an aliphatic carbon chain connecting two nucleotides, for example a C6 aliphatic chain. Thus, the modification may include incorporation of a non-nucleotide group, including incorporation into the backbone, in order to block extension by DNA polymerase.

In some embodiments, the DNA blocking position may be already modified so as to block DNA polymerase when the RT oligonucleotide is added to the transcription reaction. For example, modified nucleotide 2-amino-5-(2'-deoxy-b-D-ribofuranosyl)pyridine-5'-triphosphate (d*CTP) or 5-(2'-deoxy-b-D-ribofuranosyl)-3-methyl-2-pyridone-5'-triphosphate (d*TTP) may be used. Both modified nucleotides have been demonstrated to exhibit strong inhibition in PCR catalysed by Taq polymerase (Guo et al., 1998).

In other embodiments, the DNA blocking position may be a nucleotide or group that is modifiable upon treatment to block DNA polymerase. That is, when added to the RT reaction, the modifiable nucleotide or group is further treated in order form a modified nucleotide at the DNA blocking position.

For example, in one embodiment the modifiable nucleotide is a dU nucleotide, which is treated with uracil-DNA glycosylase (UDG). In another embodiment, the modifiable nucleotide may be a ribonucleotide, which is treated with RNase. In both cases, the modification treatment results in a modified nucleotide, including cleavage of the RT oligonucleotide, effectively preventing extension by DNA polymerase.

The modification of the modifiable oligonucleotide is performed prior to the amplification reaction, and may be performed after the RT reaction.

The stem loop portion may be of any suitable length to provide the stem-loop structure during reverse transcription and to melt during the amplification reaction. For example, the entire stem loop structure may be from 12 to 24 nucleotides in length. In some embodiments the stem portion of the stem-loop may be 4 or 6 nucleotides in length. In some embodiments, the loop portion of the stem-loop may be from 4 to 12 nucleotides in length. Design of oligonucleotides that form a stem loop structure is known, and computer programs that will calculate annealing temperature for a given sequence or that will design a stem-loop structure for certain annealing conditions are available, for example MFOLD software. As indicated above, the sequence of the stem portion may be designed to anneal at the temperature used for the reverse transcription reaction but to melt at a temperature used for the amplification reaction.

As indicated above, the RT oligonucleotide includes a target annealing portion. The target annealing portion is located 3' to the stem-loop portion and is designed to be complementary to a downstream portion of the target RNA. In some embodiments the target annealing portion of the RT oligonucleotide is 5 to 15 nucleotides in length.

Thus, following the reverse transcription reaction, the reverse transcription product is produced, the reverse transcription product comprising the RT oligonucleotide at the 5' end of the RT product, and an extended region 3' to the RT oligonucleotide that is complementary to a downstream portion of the target RNA, downstream of (or located 3' to) the region to which the target annealing portion of the RT oligonucleotide is complementary.

An amplification reaction is performed on the reverse transcribed sample.

The PCR methods used may include real-time PCR methods, as are known in the art. Such methods involve the use of a fluorescent probe to detect the amplification product as it is produced.

As will be appreciated, the amplification reaction is conducted using a pair of amplification primers, a forward primer and reverse primer.

The first amplification primer (i.e. forward primer) is designed to anneal to a downstream portion of the 3' extended region of the RT product. The primer may be any suitable length to anneal to the desired portion of the 3' extended region of the RT product. The length of the primer may be partly determined by the annealing temperature and conditions chosen. The design of amplification primers for annealing to a desired sequence within a template nucleic acid is known. In some embodiments the first amplification primer is from 12 to 27 nucleotides in length.

The second amplification primer (i.e. reverse primer) is designed to anneal to an interface portion of a DNA strand complementary to the RT product. The interface portion of the complementary DNA strand includes a region that is complementary to point where the RT product transitions from the RT oligonucleotide into the 3' extended portion. Thus, the interface portion comprises a region that is complementary to a 3' portion of the RT oligonucleotide and a 5' portion of the 3' extended region in the RT product. In some embodiments, the second amplification primer is designed to anneal to a sequence complementary to 13 to 24 nucleotides of the stem-loop portion of the RT oligonucleotide, 5 to 15 nucleotides of the target annealing portion of the RT oligonucleotide and 1 to 5 nucleotides at the 5' end of the 3' extended region of the reverse transcription product. In some embodiments, the second amplification primer is from 13 to 24 nucleotides in length.

In some embodiments, including where the RNA is an miRNA, the distance in the sequence of the amplification product between the position of the 3' end of the first amplification primer when annealed to the reverse transcription product and the position of the 3' end of the second amplification primer when annealed to the DNA strand is from −4 to 5 nucleotides, meaning there may be an overlap of from 1 to 4 nucleotides between where the 3' end of the first amplification primer anneals to the RT product and where the 3' end of the second amplification primer anneals to the DNA strand that is complementary to the RT product, or there may be a gap of from 1 to 5 nucleotides, or there may be an alignment between the 3' ends of the amplification primers when annealed on the respective template nucleic acids.

Either or both of the amplification primers may have a nucleotide that displays thermal stability when hybridized to DNA as the 3' terminal nucleotide. Inclusion of such a thermal stable nucleotide allows for use of an increased melting temperature, resulting in preferential, annealing of the amplification primer to the DNA as compared to DNA that does not include such a nucleotide. For example, the nucleotide that displays thermal stability when hybridized to DNA may be locked in an N-type furanose conformation.

The amplification reaction is performed and yields an amplification product.

Once the amplification has been produced, it is then detected.

Detecting the amplification product may involve any method of detecting, including for example hybridizing the amplification product with a microarray having immobilized complementary sequences, size separating using techniques such as gel electrophoresis or using real-time PCR methods to detect the amplification product as it is being produced.

Detecting may comprise detecting the amplification product with a fluorescent intercalating dye. For example, the fluorescent intercalating dye may be SYBR GREEN™ (N',N'-dimethyl-N-[4-[(E)-(3-methyl-1,3-benzothiazol-2-ylidene)methyl]-1-phenylquinolin-1-ium-2-yl]-N-propyl-propane-1,3-diamine).

In one embodiment exemplary of the method, there is provided a method for detecting a target miRNA molecule in a sample, the method comprising: reverse transcribing a sample containing the target miRNA using an RT oligonucleotide, the RT oligonucleotide comprising a stem-loop portion containing a dU nucleotide and a target annealing portion that is complementary to a downstream portion of the target miRNA, the target annealing portion located 3' to the stem-loop portion, to produce a reverse transcription product that comprises the RT oligonucleotide and a 3' extended region; modifying the dU nucleotide by, treatment with uracil-DNA glycosylase; amplifying the sample containing the reverse transcription product using (i) a first amplification primer that anneals to a downstream portion of the 3' extended region of the reverse transcription product and (ii) a second amplification primer that anneals to an interface portion of a DNA strand complementary to the reverse transcription product, the interface portion comprising a region that is complementary to a 3' portion of the RT oligonucleotide and a 5' portion of the 3' extended region in the reverse transcription product, to produce an amplification product; and detecting the amplification product; wherein the stem-loop portion adopts a stem-loop structure under conditions used for the reverse transcribing but does not adopt the stem-loop structure under conditions used for the amplifying.

The present methods are further exemplified by way of the following non-limiting example.

EXAMPLES

Example 1

High Performance Quantification of Mature MicroRNAs by Real-Time RT-PCR Using Deoxyuridine-Incorporated Oligonucleotides and Hemi-Nested Primers Materials and Methods Mature and Precursor miRNA Templates and Sequence Analysis.

Mature miRNAs were synthesized by Proligo (Sigma, St Louis, Mo., USA) or Integrated DNA Technologies (Coralville, Iowa, USA). T7 promoter sequenced tagged PCR primers were used to clone precursor miRNAs (Table 2). The purified PCR products were validated by sequencing and subjected to MEGAscript T7 Transcription kit (Ambion, Austin, Tex., USA) for in vitro transcription of precursor miRNAs according to manufacturer's instructions. Both mature and precursor miRNAs were quantified by spectrophotometry and diluted to desired concentration to serve as standards. Sequence alignment and phylogenetic analysis of miRNA homologs were performed using Vector NTI software version 8.0 (Invitrogen, Carlsbad, Calif., USA).

Cell Culture and Total RNA Isolation.

Human glioblastoma cell lines A172 and U251 were cultured in DMEM supplemented with 10% fetal bovine serum (FBS, Sigma) and antibiotics (100 U/ml penicillin and 100 µg/ml streptomycin) in a 5% CO2 humidified incubator at 37° C. U251 cells were seeded at 200,000 cells per well in E-well plate for 24 h and incubated with FBS-free DMEM medium for 12-16 h. The cells were then stimulated with 100 ng/ml of GDNF for defined periods of time in DMEM. For MEK inhibitor studies, the cells were pre-incubated with 5 μM U0126 (Promega, Madison, Wis., USA) for 45 min in DMEM prior to GDNF stimulations. Total RNA from untreated or GDNF treated glioblastoma cells was isolated using TRIzol reagent (Invitrogen) in the presence of 20 μg/ml linear acrylamide (Ambion) according to the manufacturer's instructions. The extracted RNA samples were then quantified using spectrophotometry and the integrity examined by denaturing RNA gel electrophoresis.

Reverse Transcription (RT).

Total RNA samples were treated with RNase-free DNase I (Promega) at 37° C. for 30 min. The DNase was inactivated at 80° C. for 5 min. For RT of primary and precursor miRNAs, 100 ng of DNase I treated total RNA or dilutions of in vitro transcribed precursor miRNA standards were initially heated at 80° C. in the presence of 150 nM of gene specific reverse primers for 5 min, snapped chilled on ice and reverse transcribed [1× buffer, dNTPs (10 mM), dithiothreitol (DTT), RNase inhibitor, Thermoscript (15 U)] as specified by the manufacturer (Invitrogen). The reverse transcription was carried out at 60° C. for 45 min and terminated by a further incubation at 85° C. for 5 min. For the detection of precursors, both RT and real-time PCR were carried out with pre-validated gene-specific primers as reported previously (Jiang et al., 2005).

For RT of mature miRNAs, 100 ng of DNase I treated total RNA or dilutions of synthetic human mature miRNA standards were reverse transcribed using 100 U of Improm II (Promega) and 100 nM of either stem-loop or linear RT oligonucleotide in a total volume of 10 μl for 30 min at 42° C. The reaction was terminated by heating at 70° C. for 5 min. For multiplex RT of 24 mature miRNAs, 100 ng of DNase I treated total RNA samples were reverse transcribed using 400 U of Improm II and 100 nM of each RT oligonucleotide (2.4 μM of total) in a total volume of 40 μl for 30 min at 42° C. The cDNA samples were then used for real-time PCR using miRNA-specific primers. Primers for both RT and real-time PCR were listed in Table 3. Linear RT oligonucleotides were listed in Table 4.

Uracil DNA Glycosylase (UDG) Treatment.

RT oligonucleotides with deoxyuridine (dU) incorporation were synthesized by Integrated DNA Technologies. Reverse transcription was performed as described above. The cDNA samples were then treated with 5 U UDG (New England Biolabs, Beverley, Mass., USA) at 37° C. for 10 min. The reaction was inactivated at 95° C. for 10 min and subjected to real-time PCR.

Detection of miRNA without RNA Isolation.

U251 cells in 96-well plate at various cell densities (10 to $10^5$ cells per well) were washed once with PBS, lysed and reverse transcribed directly in the wells with 40 μl of RT mixture containing 0.5% Triton X-100 (Thermo Fisher Scientific, MA, USA), 400 U Improm II (Promega) and 100 nM of each RT oligonucleotide (2.4 μM of total) in the presence or absence of RNase inhibitor SUPERase-In (1 U/μl, Ambion) for 30 min at 42° C. For comparison, total RNA from the identical densities of cells were isolated and reverse transcribed in the same RT mixture. The cDNA samples were then used for real-time PCR.

Real-Time PCR.

Real-time PCR was performed on the CFX96 system (Bio-Rad, Hercules, Calif., USA) using SYBR GREEN™ I.

Real-time PCR for precursor miRNA and U6 snRNA was performed according to previous reports (Schmittgen et al., 2004; Jiang et al., 2005). Fast thermo-cycling of miRNA cDNAs was performed after 10 min initial denaturation at 95° C. followed by 50 cycles of 5 s denaturation at 95° C. and 5 s annealing/extension at 60° C. One μl of each cDNA sample was subjected to realtime PCR in a total volume of 25 μl in 1× XtensaMix-SG™ (BioWORKS, Singapore), containing 2.5 mM MgCl2, 100 nM of each primer and 1.25 U KlearTaq DNA polymerase (KBiosciences, Hoddesdon, UK). The threshold cycles (Ct) were calculated automatically using the CFX manager software (Bio-Rad). Where applicable, all miRNA expression levels were normalized to U6 snRNA expression.

Calculation of Real-Time RT-PCR Assay Efficiency and Specificity.

Efficiency and specificity of real-time RT-PCR were determined as previously described (Too, 2003). Briefly, 10-fold dilutions of miRNA were subjected to real-time RT-PCR. Standard curve of the miRNA were obtained by plotting Ct vs Log(copies) of synthetic miRNA dilutions. Assay efficiency was calculated by $(10^{1/S}-1) \times 100\%$, where S was the slope of the standard curve. For calculation of specificity, identical amounts ($10^9$ copies per RT) of perfectly matched miRNA and mis-matched miRNAs were quantified by real-time RT-PCR. ΔCt was then calculated as $Ct_{perfectly\ matched\ miRNA} - Ct_{mis-matched\ miRNA}$. Relative detection of mis-matched miRNAs was then calculated by $10^{\Delta Ct/S} \times 100\%$.

Results

Overview of Hemi-Nested Real-Time RT-PCR Assay.

Figure 5:
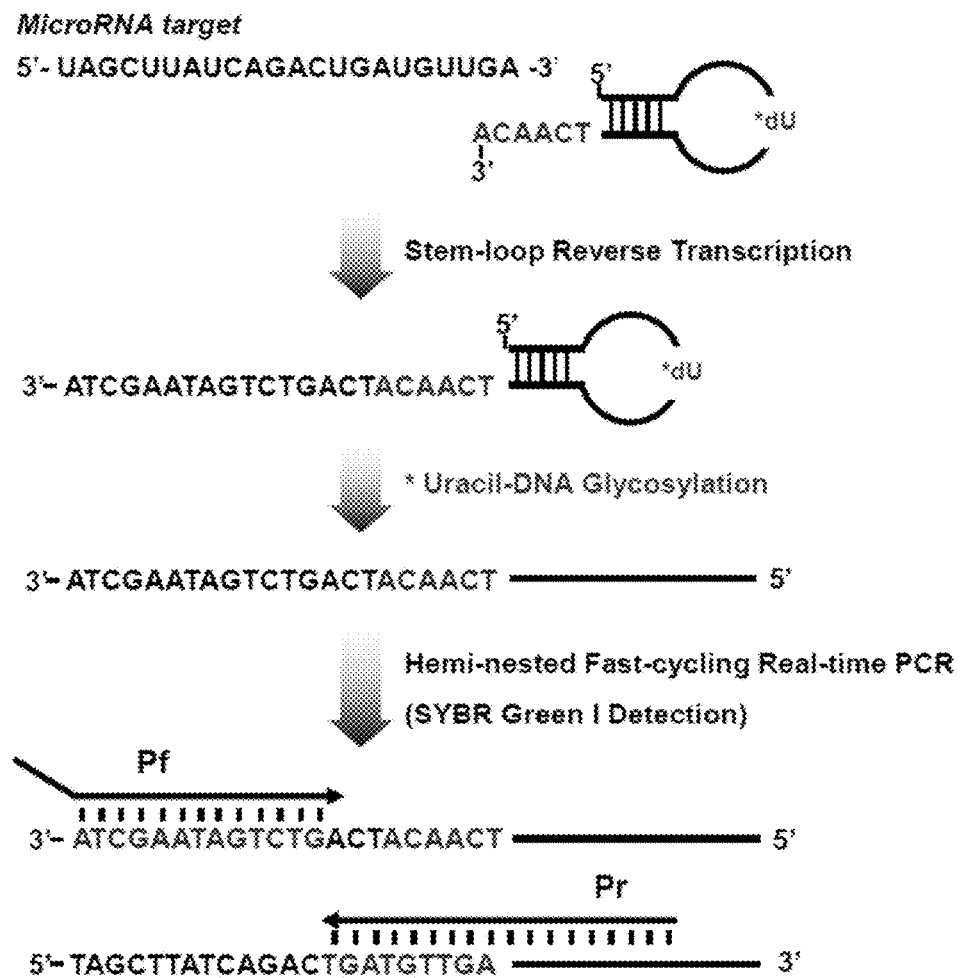
FIG. 5. Schematics for the design of a hemi-nested real-time RT-PCR assay. Pf, forward primer; Pr, reverse primer. The primer sequences shown correspond to SEQ ID NOs. 110-112 as shown in FIG. 25 (Table 5).

In the present study, we have designed a simple method for specific detection of mature miRNAs by hemi-nested real-time RT-PCR (FIG. 5). Initially, we noticed that in a number of previous reports (Chen et al., 2005; Raymond et al., 2005; Shi & Chiang, 2005; Duncan et al., 2006; Varkonyi-Gasic et al., 2007; Sharbati-Tehrani et al., 2008; Yang et al., 2009), the reverse PCR primers were designed to anneal directly to sequences in the RT oligonucleotide. To achieve specificity, a unique miRNA-specific fluorescent probe is required to discriminate the targets from nonspecific amplicons (Chen et al., 2005). In the case of some TaqMan-based assays, this specificity was compromised for the convenience of throughput by using one common probe for detection. We hypothesized that increased specificity can be achieved by designing a hemi-nested reverse PCR primer instead of using a common or universal reverse PCR primer. FIG. 6 demonstrates the design of the forward and reverse primers in this method with different distances between the 3' ends of each primer on the double-stranded template. FIG. 7 shows that a smaller loop of 4 nucleotides is as effective as a larger loop of 12 nucleotides.

Figure 8:
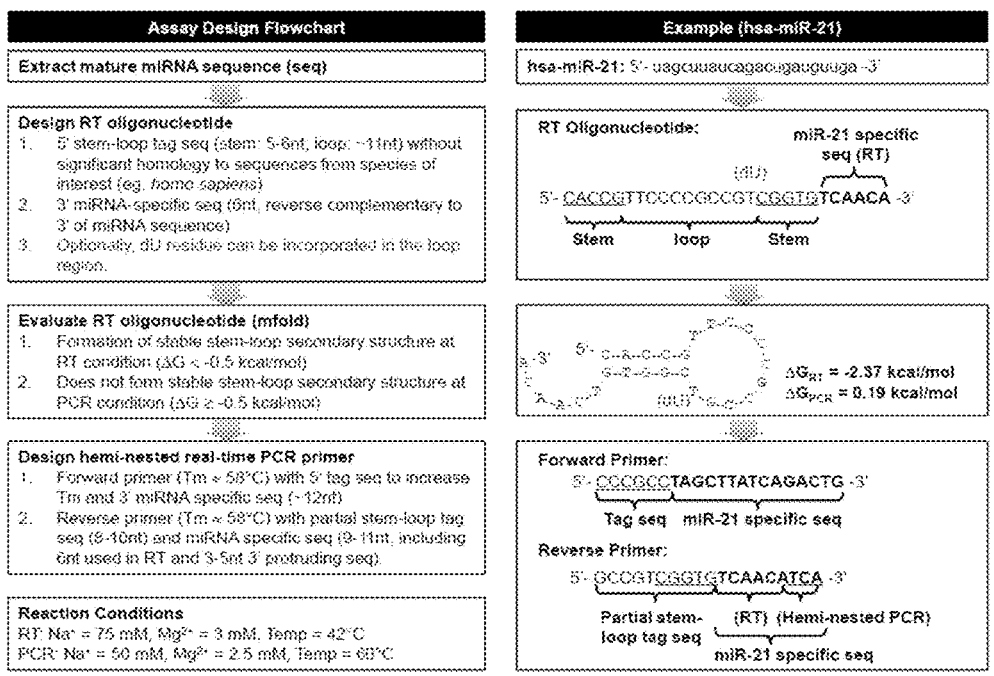
FIG. 8. Flow Chart and example for designing hemi-nested real-time RT-PCR assay. The primer sequences shown correspond to SEQ ID NOs. 110 and 113-115 as shown in FIG. 25 (Table 5).

To test this hypothesis, mature miRNA was first reverse transcribed at 42° C. by RT oligonucleotide which adopted a stable stem-loop secondary structure during RT. The cDNA sample was then amplified using a tagged forward primer (Pf) and a hemi-nested reverse primer (Pr), where 3-5 nucleotides extend beyond the RT oligonucleotide. Amplification of the cDNA sample was monitored in real-time PCR using SYBR GREEN™ I. RT oligonucleotide can be incorporated with deoxyuridine (dU) residues and the cDNA generated was subsequently treated with Uracil-DNA Glycosylase (UDG) at 37° C. before amplification. To assist in the user defined designs of any real-time RT-PCR assays, a flow chart was presented in using hsa-miR-21 (hereafter miR-21) as an example (FIG. 8).

Performance of the Hemi-Nested Real-Time RT-PCR Assay.

Figure 9:
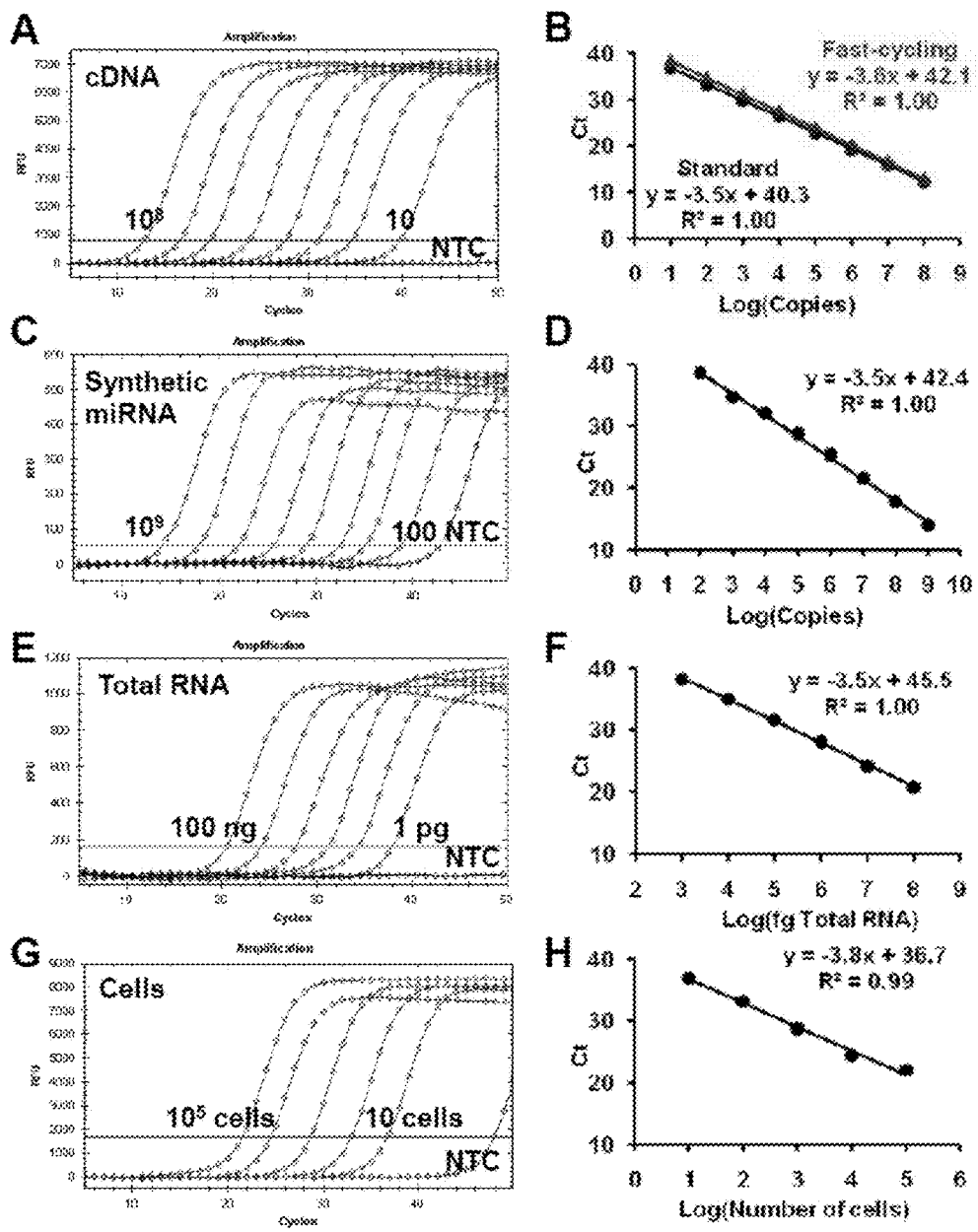
FIG. 9. Performance of miR-21 hemi-nested real-time RT-PCR assay. (A, B) miR-21 cDNA ($10^8$ to 10 copies) were amplified by real-time PCR assay under fastcycling conditions compared to standard cycling protocol. (C, D) Dilutions of synthetic miR-21 miRNA ($10^9$ to $10^2$ copies), (E, F) dilutions of total RNA from A172 cells (100 ng to 1 pg) and (G, H) total RNA isolated from dilutions of U251 cells (100,000 to 10 cells) were reverse transcribed with miR-21 RT oligonucleotide. The cDNA samples (10% v/v) were amplified by real-time PCR along with non-template control (NTC). Amplification plots (A, C, E, G) and standard curves (B, D, F, H) of the assay were shown. Standard curves were plotted as Ct versus Log (starting material per RT).

The performance of the hemi-nested real-time PCR assay was first evaluated using miR-21 cDNA dilutions under both fast (10 s per cycle) and standard (75 s per cycle with 15 s denaturation and 60 s annealing/extension) thermo-cycling profiles. The assay exhibited excellent dynamic range and linearity under both cycling profiles (FIG. 9A,B), demonstrating the robustness of this assay for rapid detection of miRNAs. To evaluate the performance of both RT and PCR, synthetic miR-21 was diluted over 7 orders of magnitude ($10^9$ to $10^0$ copies per RT) and quantified by hemi-nested realtime RT-PCR. Excellent linearity of the standard curve suggested that the miR-21 assay had a wide dynamic range of at least 7 logs and was able to detect as few as 100 copies (subzeptomoles) per RT reaction (FIG. 9C,D).

Figure 10:
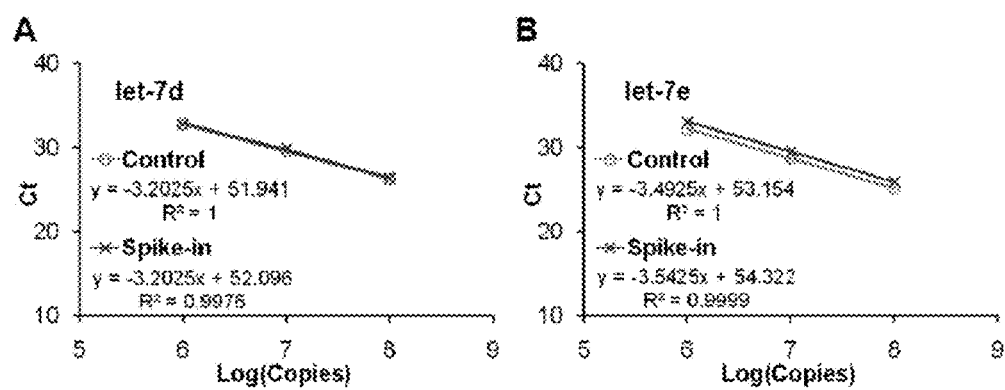
FIG. 10. Quantification of synthetic let-7d and let-7e miRNA dilutions with U251 total RNA spike-in. Standard dilutions ($10^9$, $10^8$ and $10^7$ copies) of synthetic let-7d (A) or let-7e (B) were spiked with 100 ng of total. RNA isolated from U251 cells. Control miRNA dilutions or total RNA spiked-in miRNA dilutions were reverse transcribed with let-7d or let-7e RT primers. The cDNA samples (10% v/v) were amplified by real-time PCR. Standard curves were plotted as Ct versus Log (input cDNA per PCR reaction).

We next examined the performance of this assay in detecting miRNA from total RNA samples. Total RNA dilutions from 100 ng to 1 pg (FIG. 9E,F) and total RNA isolated from 100,000 to 10 cells (FIG. 9G,H) were quantified using miR-21 heminested real-time RT-PCR assay. The standard curves again showed excellent linearity (FIG. 9F,H), suggesting that this assay was capable of reliably detecting miRNAs from a minute amount (1 pg) of total RNA or from as few as 10 cells. The capability of this assay in quantifying mature miRNA from total RNA without RNA fractionation was further supported by total RNA spike-in experiments. Here, 100 ng of total RNA from U251 cells, which did not contain let-7d and let-7e (data not shown), was spiked with varying amounts of synthetic let-7d or let-7e miRNAs. The presence of total RNA did not affect the quantification of mature let-7d/let-7e miRNAs (FIG. 10).

Figure 12:
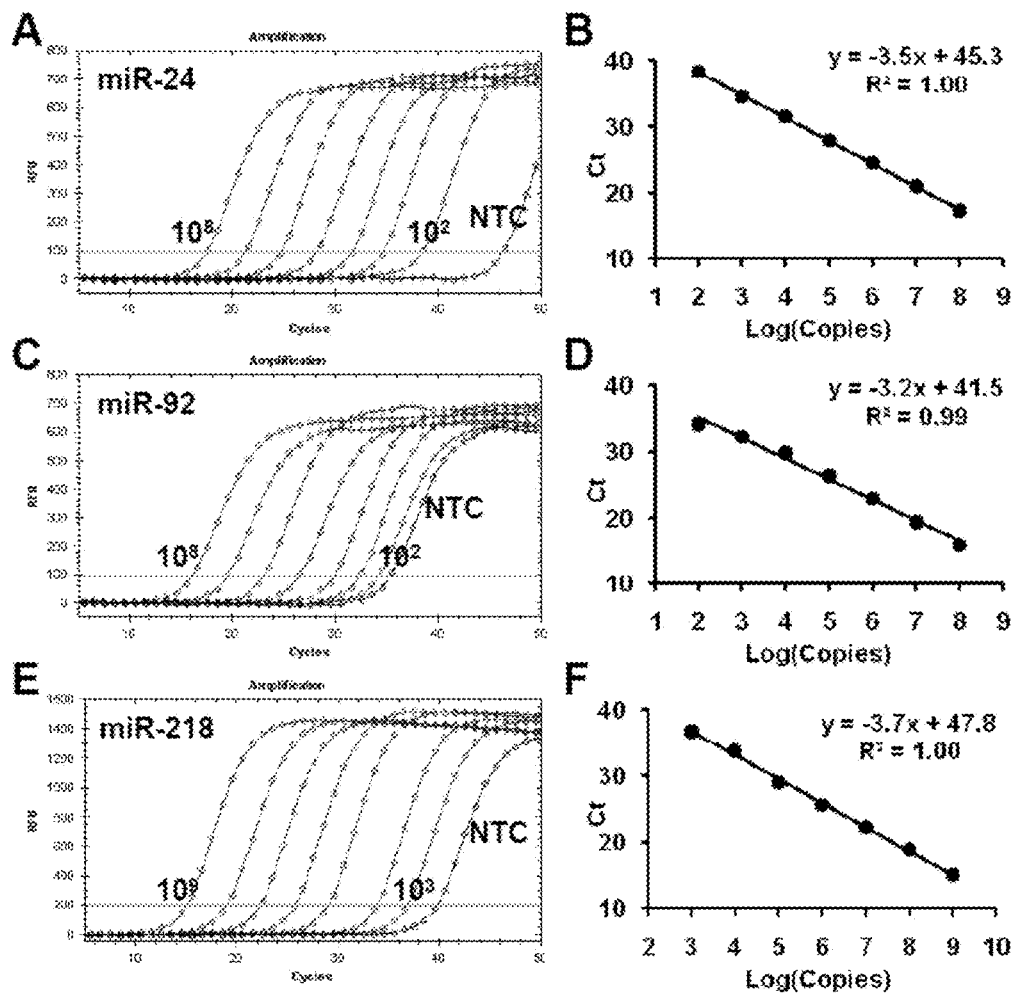
FIG. 12. Dynamic range and efficiency of miR-24 (A, B), miR-92 (C, D) and miR-218 (E, F) real-time RTPCR assays. Standard dilutions of synthetic miR-24, -92 and -218 were reverse transcribed with miRNA-specific RT oligonucleotide. The cDNA samples (10% v/v) were amplified by real-time PCR along with non-template control (NTC). Amplification plots (A, C, E) and standard curves (B, D, F) of the assay were shown. Standard curves were plotted as Ct versus Log (input cDNA per PCR reaction).
Figure 14:
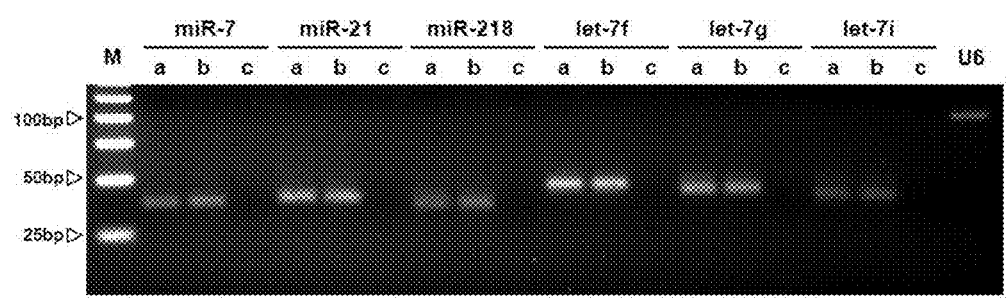
FIG. 14. Gel electrophoresis of miRNA real time RT-PCR products. Real time RT-PCR assays were performed with $10^6$ copies of synthetic miRNA (a), 10 ng U251 total RNA (b) or non-template control (c). U6 was amplified from 10 pg of U251 total RNA. The amplified products and the 25 bp marker (M) were resolved by 4% agarose gel. Product sizes: miR-7 (37 bp), miR-21 (38 bp), miR-218 (36 bp), let-7f (45 bp), let-7g (42 bp), let-7i (38 bp) and U6 (94 bp).

Hemi-nested real-time RT-PCR assays for three other miRNAs (miR-24, miR-92 and miR-218) were also evaluated (FIG. 12). All the three assays showed excellent dynamic range (at least 7 logs), sensitivity ($10^3$-$10^4$ copies per RT) and RT-PCR efficiency (88%-100%). Furthermore, these assays showed specific amplifications of target miRNAs from both synthetic standards and total RNA samples. The sizes of the amplicons were verified by gel electrophoresis (FIG. 14).

Specific Detection of Mature Against Precursor miRNAs.

The capability of the hemi-nested real-time RT-PCR assay in discriminating mature against precursor miRNAs were investigated using 9 mature miRNAs and their corresponding precursors (miR-21, miR-7-1, miR-7-2, miR-218-1, miR-218-2, let-7f-1, let-7f-2, let-7g, let-7i). For comparison, we have also evaluated linear RT oligonucleotides that do not form favorable secondary stem-loop structures during RT ($\Delta G \geq -0.5$ kcal/mol). For better comparison, these stem-loop RT oligonucleotides and their corresponding linear RT oligonucleotides were designed to 1) differ by only 4-5 bases at the 5' end; 2) have identical GC content and similar Tm (<1° C. difference) and 3) have identical 3' sequence so that same primers can be used in PCR.

The same amount ($10^9$ copies per RT) of mature miRNAs and pre-miRNAs were individually quantified using either stem-loop or linear RT and hemi-nested real-time PCR. Depending on the 9 pre-miRNAs examined, mature miRNAs were detected 3-14 cycles (average $\Delta Ct$ of 8.7 cycles) earlier than pre-miRNAs using stem-loop RT oligonucleotides. In contrast, the assays using linear RT oligonucleotides were less discriminative (average $\Delta Ct$ of 4.8 cycles) and failed in discriminating some mature miRNAs from their precursors such as pre-miR-21, pre-let-7f-1 and pre-let-7i (Table 1).

Discrimination of Human let-7 miRNA Homologs.

Several miRNA families (eg. hsa-let-7, hsa-miR-30) consist of highly homologous miRNAs which differ by only a single or a few nucleotides. The eight let-7 family miRNAs share up to 63.6% overall sequence identity, among which let-7a and let-7c, let-7a and let-7f, let-7b and let-7f differ only by a single nucleotide (FIG. 11A). In this study, hemi-nested real-time RT-PCR assays for each let-7 miRNA were designed.

Each assay was used to amplify all eight synthetic let-7 miRNAs and the relative detection was compared. Briefly, specific reverse transcription of each let-7 miRNA ($10^9$ copies per RT) was first achieved using stem-loop RT oligonucleotide targeting the less homologous 3' region. Discrimination of let-7 miRNAs was further improved by a miRNA-specific forward PCR primer and a hemi-nested reverse primer preferably with miRNA-specific 3'-terminal sequence. All of the eight let-7 assays showed excellent discrimination against homologous miRNAs with less than 1% nonspecific detection, except for let-7a assay with 1.778% relative detection against let-7c (FIG. 11B). For let-7 miRNAs that differ by 2 nucleotides or more, these assays were able to specifically detect the target miRNA with less than 0.3% cross-target amplification. This result suggests that the hemi-nested real-time RT-PCR assay was capable of discriminating highly homologous miRNAs at levels comparable to fluorescent probe-based real-time RT-PCR assays (Chen et al., 2005), with inexpensive SYBR GREEN™ I detection chemistry.

Improved Assay Performance by dU-Incorporated RT Oligonucleotide and UDG Treatment.

Figure 13:
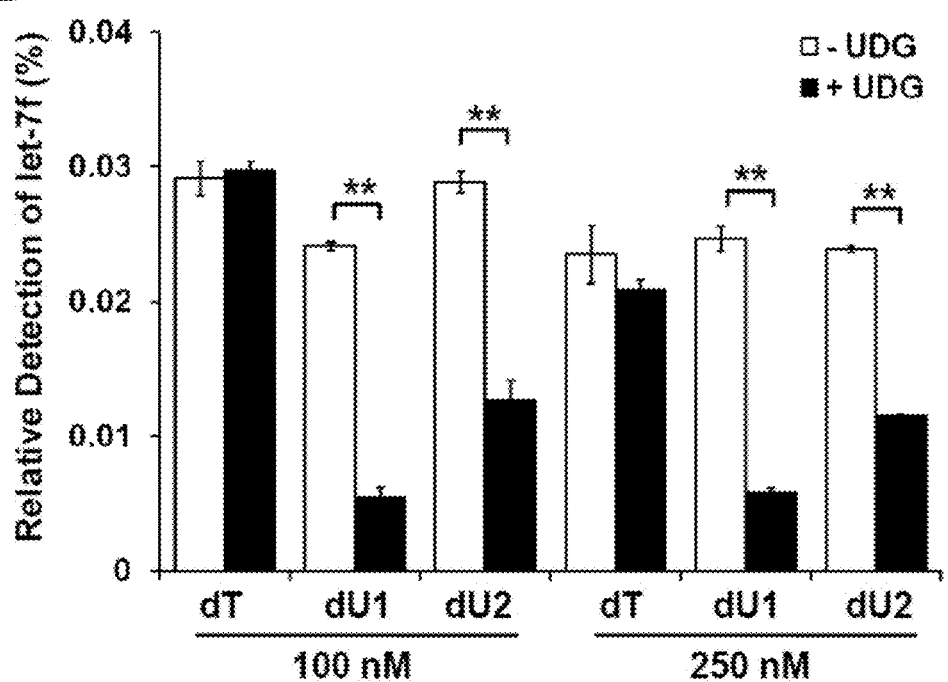
FIG. 13. Specificity of hemi-nested real-time RT-PCR assay using dU-incorporated RT oligonucleotides. A) Sequence comparison of dT and dU RT oligonucleotides. The dU residues are underlined. B) Relative detection of let-7f miRNA by let-7a assay. $10^9$ copies of let-7a or let-7f were reverse transcribed using 100 nM or 250 nM of dT, dU1 or dU2 RT oligonucleotide. The cDNA samples (10% v/v) were treated with or without UDG and amplified using let-7a specific PCR primers. Non-specific amplification of let-7f miRNA was calculated and expressed as % of relative detection. Error bars indicate standard deviations of quadruplicate measurements. Significant differences in relative detection between UDG-treated and non-treated samples were calculated by Student's t-test. **$p<0.001$. The primer sequences shown correspond to SEQ ID NOs. 124-126 as shown in FIG. 25 (Table 5).
Figure 16:
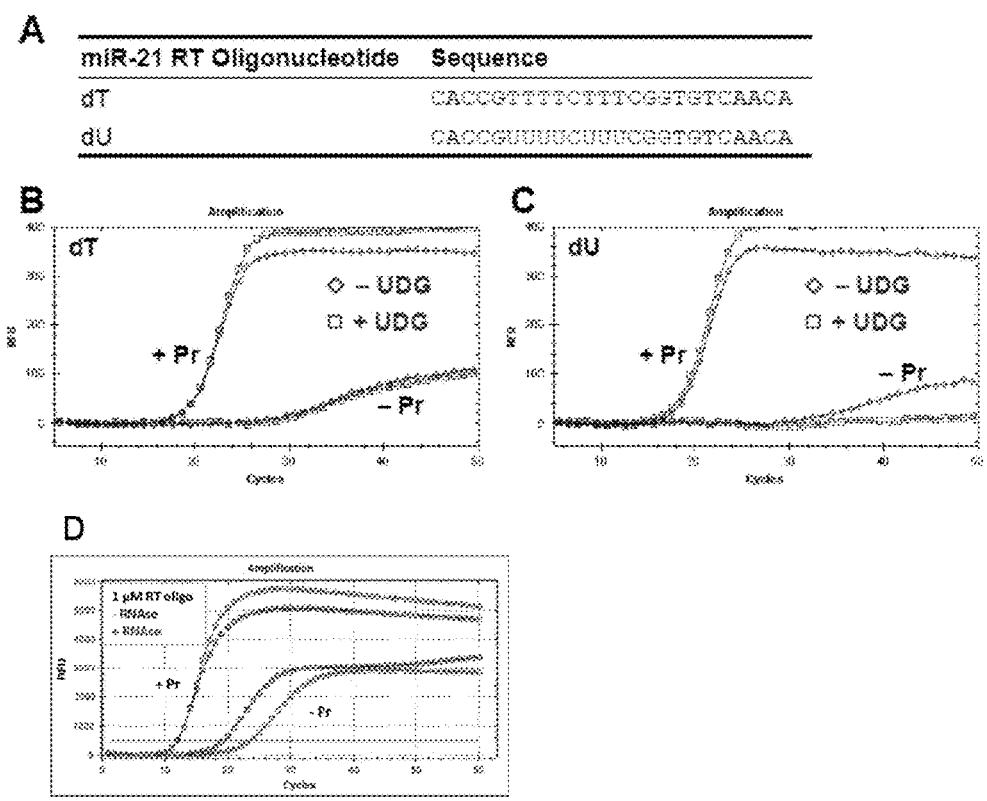
FIG. 16. UDG treatment of dU-incorporated RT oligonucleotide prevented it from serving as PCR primer after RT. A) Sequence of standard (dT) and dU-incorporated (dU) RT oligonucleotides for miR-21. Synthetic miR-21 ($10^9$ copies) were reverse transcribed with of dT (B) or dU (C) RT oligonucleotides. The cDNA samples (10% v/v) were then treated with (red amplification curves) or without UDG (blue amplification curves) and subjected to real-time PCR with both forward and reverse primers (+Pr) or forward primer alone (−Pr). D) RT oligonucleotide with RNA sequences in the loop with or without treatment with RNAse. The primer sequences shown correspond to SEQ ID NOs. 127 and 128 as shown in FIG. 25 (Table 5).

Discrimination between certain highly homologous miRNAs can be further improved using a novel strategy involving uracil-DNA glycosylase (UDG) treatment. In this study, we observed that the amount of RT oligonucleotides carried-over was able to serve as amplification primers during PCR, although with poorer efficiency (FIG. 16). Interestingly, after treatment with UDG, dU-incorporated RT (dU-RT) oligonucleotide but not standard RT (dT-RT) oligonucleotide was not able to serve as reverse PCR primer (FIG. 16B,C). We then hypothesized that discrimination between let-7 miRNA homologs may be further improved with similar strategy. Indeed, while standard (dT) RT oligonucleotide for let-7a showed relative detection of 0.03% against let-7f miRNA, let-7a RT oligonucleotides with dU incorporation at either loop (dU1) or stem (dU2) region were significantly less capable of cross-amplifying let-7f after treatment with UDG (FIG. 13). Both the let-7a dT and dU RT oligonucleotides were able to prime reverse transcription of let-7a equally well (data not shown).

Application of Multiplexed Assays to Identify GDNF-Induced miRNA Expressions in U251 Cells.

Figure 15:
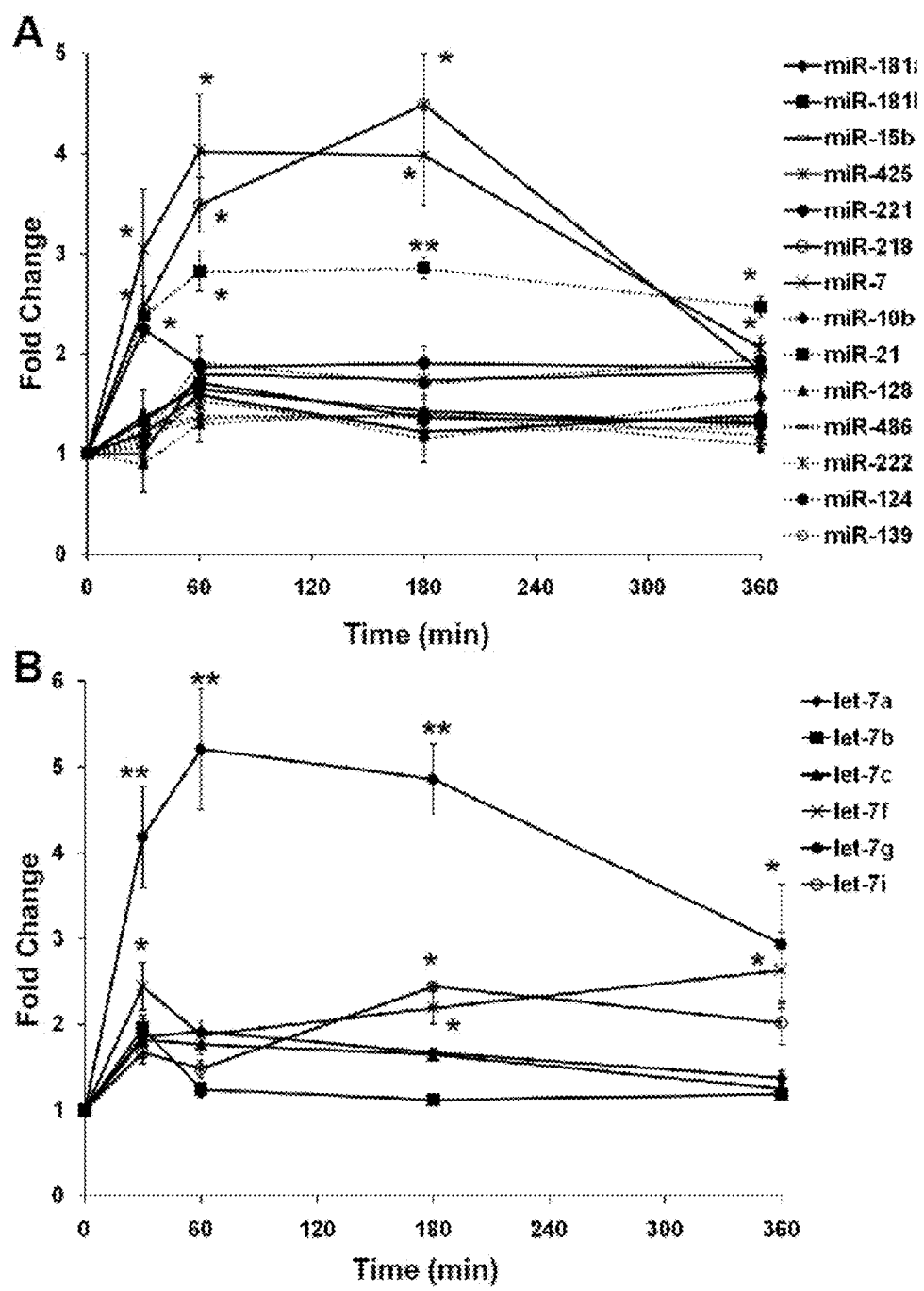
FIG. 15. GDNF regulated miRNA expressions in U251 cells. Regulation of selected mature miRNAs (A, B) were quantified by hemi-nested real-time RT-PCR and expressed as fold changes to non-stimulated control samples. Error bars indicate standard deviations of triplicate measurements. Significant differences in gene expression between treated and control samples were calculated by Student's t-test. *$p<0.01$; **$p<0.001$.
Figure 18:
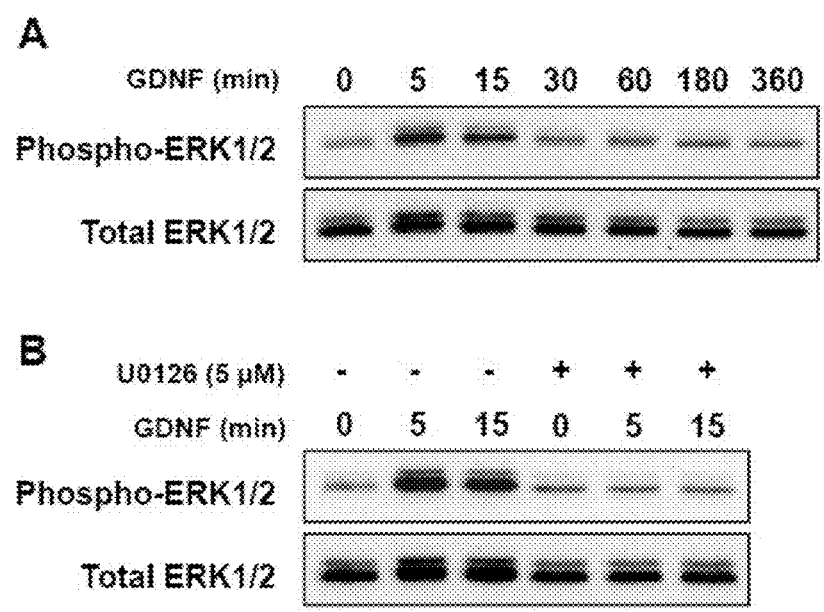
FIG. 18. GDNF-induced signaling activation in U251 human glioblastoma cells. Control and GDNF stimulated U251 cells were lysed with 2% SDS. Total protein lysates were quantified using microBCA protein assay (Pierce, Rockford, Ill., USA). Total protein (10 μg) were separated by SDS-PAGE and probed with antibodies against phospho ERK1/2 (Cell phospho-Signaling Technologies, Danvers, Mass., USA). The blots were striped in Western Blot Stripping Buffer (Pierce) and re-probed with total ERK1/2 (Cell Signaling Technologies) to verify equal loading. Chemiluminescence was imaged and analyzed by ChemiDoc system (Bio-Rad). A) Time-course of ERK1/2 MAPK activation by GDNF (100 ng/ml) in U251 cells. B) GDNF-induced ERK1/2 MAPK activation was inhibited by pre-treatment of MEK inhibitor U0126 (5 μM).

To evaluate the robustness of this miRNA detection method, hemi-nested realtime RT-PCR assays were designed and applied to identify GDNF-regulated miRNAs in U251 cells. A total of 26 miRNA were examined including 18 miRNAs (miR-7, -10b, -15b, -21, -124, -128, -137, -139, -146b, -181a, -181b, -181c, -218, -221, -222, -425, -451, -486) reported to be dysregulated in human glioblastoma (Pang et al., 2009) and the 8 let-7 family miRNAs. Twenty miRNAs (except for miR-137, -146b, -181c, -451, let-7d and let-7e) were found to be expressed in U251 cells (data not shown). Stimulation of the cells with GDNF induced time-dependent activation of ERK1/2 MAPK, which was inhibited by pretreatment of MEK inhibitor U0126 (FIG. 18). We then quantified the temporal regulation of expressions of these 20 miRNAs in U251 cells by GDNF. Interestingly, GDNF stimulation induced timedependent up-regulation of miR-7, -21, -218 (FIG. 15A) and let-7f, -7g, -7i (FIG. 15B). No significant regulation of the other miRNAs was observed.

Figure 17:
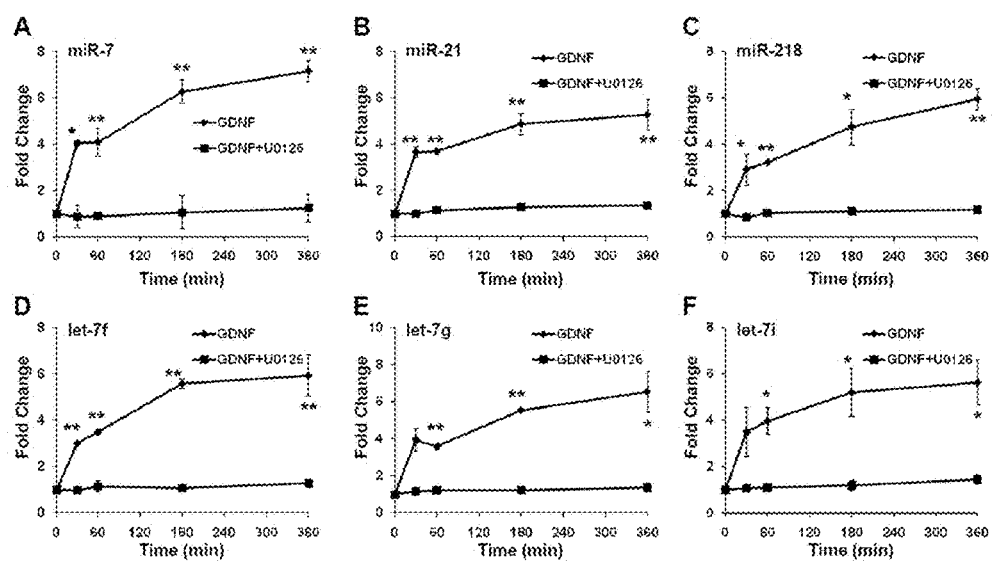
FIG. 17. Multiplexed quantification of the six GDNF regulated miRNAs. Expressions of miR-7 (A), miR-21 (B), miR-218 (C), let-7f (D), let-7g (E) and let-7i (F) was quantified by multiplexed real-time RT-PCR assays of 24 miRNAs. Regulation of these miRNAs was expressed as fold changes to non-stimulated control samples. Error bars indicate standard deviations of triplicate measurements. Significant differences in gene expression between treated and control samples were calculated by Student's t-test. *$p<0.01$; **$p<0.001$.
Figure 20:
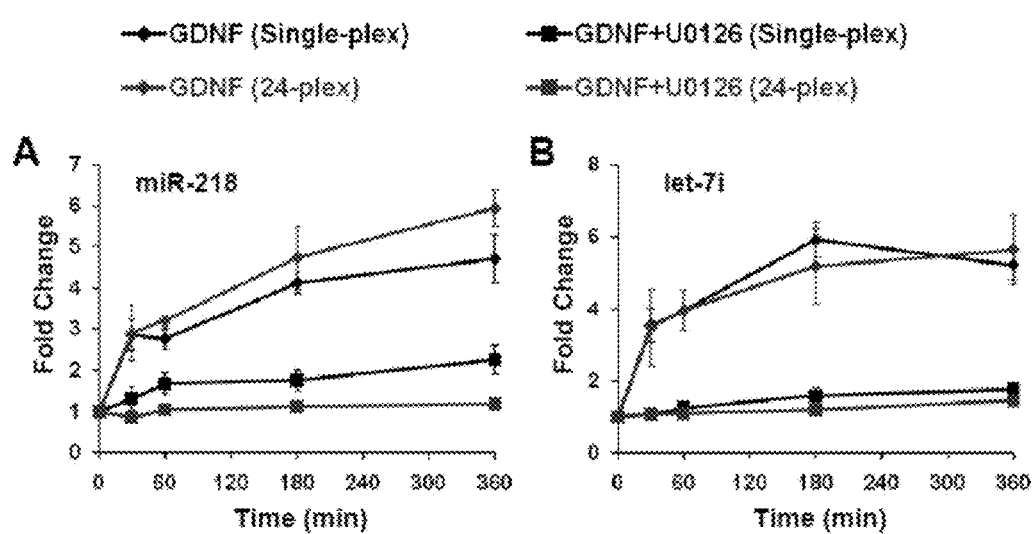
FIG. 20. Quantification of GDNF-regulated miRNAs by single-plexed and multiplexed realtime RT-PCR. Total U251 RNA samples were reverse transcribed by single miRNA-specific RT oligonucleotide (black lines) or 24-plexed RT oligonucleotides (red lines). The cDNA samples were then quantified for expressions of (A) miR 218 and (B) let 7i. Regulation of these miRNAs was expressed as fold changes to non-stimulated control samples.

We then developed a multiplexed assay for simultaneous reverse transcription of the 26 miRNAs (corresponding to 24 RT oligonucleotides) and subsequent detection of individual miRNA by hemi-nested real-time PCR. Using this 24-plex assay, we found that up-regulation of the 6 miRNAs by GDNF was effectively inhibited by pretreatment of the cells with U0126, suggesting that MEK-ERK1/2 signaling pathway was required for GDNF-induced miRNA expressions (FIG. 17). Similar result was obtained by standard single-plex assay using miR-218 and let-7i as examples (FIG. 20).

Direct and Multiplex Detection of miRNAs in Cell Lysates.

Figure 19:
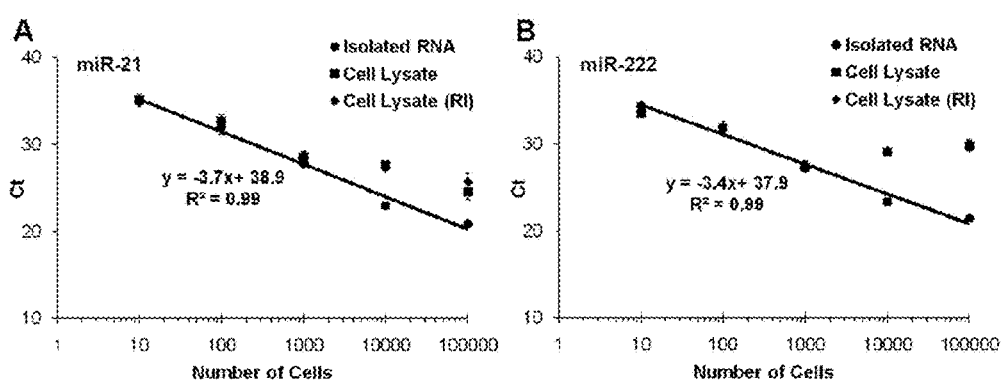
FIG. 19. Direct and multiplexed detection of miRNAs from cell lysates. U251 cells cultured in 96-wells at various density (10, 100, 1000, 10000 and 100000 cells per well) were directly lysed and reverse transcribed in reaction mixture containing 24 miRNA RT oligonucleotides. The cDNA samples (2.5% v/v) generated from isolated RNA or cell lysates were amplified by (A) miR-21 and (B) miR-222 real-time PCR assays. Standard curves for isolated RNA were plotted as Ct versus Log (cells per RT). RI; RNase inhibitor.

Direct detection of miRNA from cell lysates can avoid the time-consuming multistep RNA isolation process and dramatically increase the throughput of the assay. We then further investigated the capability of the hemi-nested real-time RT-PCR assay in direct and multiplex quantification of miRNAs from 10 to 100,000 cultured U251 cells in 96-wells. Isolated total RNA from these cells were used as controls for quantification. Similar to FIG. 9H, excellent linearity of the miR-21 and miR-222 standard curves of isolated RNA controls suggested that miRNAs can be reliably quantified from total RNA extracted from as few as 10 cells (FIG. 19). Importantly, both miR-21 and miR-222 can be detected equally well from lysates of 10-1000 cells using this multiplex assay, as compared to isolated RNA controls. However, it is worthy to note that direct quantification of miRNAs was compromised with lysates from near confluent ($10^4$ cells/well) or over confluent cell densities ($10^5$ cells/well). Interestingly, no significant difference was observed in detection of miRNAs from cell lysates with or without RNase inhibitors, suggestive of remarkable stability of mature miRNAs.

Discussion

It is now known that miRNAs play important roles in modulating gene expression and it has been suggested that up to 60% of human genes are targeted by miRNAs (Friedman et al., 2009). With the increase interest in the expression profiles of miRNAs, rapid, robust and cost-effective methods for the detection of mature miRNAs are highly desirable. The hemi-nested real-time RT-PCR assays described herein were simple to design and showed excellent performance and provided the flexibility for the design of any miRNAs that may be identified in the future.

With synthetic miRNA targets, the hemi-nested real-time RT-PCR assay showed wide dynamic range of at least 7 logs, high sensitivity of as few as 100 molecules per RT (subzeptomoles) and high RT-PCR efficiency of greater than 90%. Besides relative quantification of miRNA expression, the synthetic miRNA standards could also allow absolute quantification of miRNA expression from total RNA samples. In contrast to previously reported miRNA real-time PCR assays which were performed under standard thermo-cycling profile of 45 to 75 s per cycle (Chen et al., 2005; Raymond et al., 2005; Shi & Chiang, 2005; Sharbati-Tehrani et al., 2008; Yang et al., 2009), our assay was capable of fast thermo-cycling (10 s per cycle) without modification of reaction mixtures. The fast-cycling capability of this assay may in part be attributed to the short amplicon (<50 bp) generated by hemi-nested primers and rapid fluorescence acquisition of SYBR GREEN™ I without the necessity of probe hydrolysis.

Specific and sensitive quantification of mature miRNA from total RNA samples usually requires size-fractionation and pre-amplification, respectively. It has been reported that besides additional sample handling steps, size-fractionation can result in consistent loss of miRNAs (Wang et al., 2007) and pre-amplification efficiency is significantly affected by number of A bases in miRNAs (Mestdagh et al., 2008). With our miRNA quantitative assay, small amounts of total RNA (1 pg to 100 ng) and total RNA isolated from as few as 10 cells can be efficiently detected without the need for fractionation or pre-amplification. Previously, Megaplex miRNA assays for simultaneous reverse transcription of 220 to 450 miRNAs has been applied to quantify miRNA expression from minute amount of total RNA or single cell (Tang et al., 2006; Mestdagh et al., 2008). Because much lower concentration of RT oligonucleotide was used for each miRNA, pre-amplification was required prior to real-time PCR especially when starting total RNA is less than 350 ng. In this study, we have shown that multiplex of 24 miRNAs resulted in conclusions comparable to single-plexed assays without reduction of RT oligonucleotide concentration or the necessity of pre-amplification. Therefore, we suggest that multiplex of relatively small number of miRNAs with this method could reduce sample and reagent requirement and yet allow reliable quantification of miRNAs. These multiplexed assays can further be used for direct quantification of miRNAs from cultured cells in 96-wells. Therefore, the method reported herein is capable of reliable, rapid and high throughput quantitative profiling of miRNA expressions not only from minute amounts of isolated RNAs but also directly from lysed cells without the need for laborious, time consuming methods of RNA isolation.

In this study, specific detection of mature miRNAs from precursors is achieved by RT oligonucleotides with stem-loop secondary structure. Although the expression levels of precursor miRNAs often correlate with mature miRNAs (Calin et al., 2004; Schmittgen et al., 2004), it is not uncommon that maturation of miRNA can be regulated whereby precursor miRNAs were expressed but their mature forms were undetectable (Ambros et al., 2003; Michael et al., 2003; Wulczyn et al., 2007; Schmittgen et al., 2008). In order to discriminate between the regulations of miRNA processing and maturation, specific assays for both mature and precursor miRNAs are highly desirable. We found that stem-loop but not linear RT oligonucleotides preferentially reverse transcribed mature but not precursor miRNAs. The stem-loop strategy has been previously applied successfully for specific reverse transcription of sense strand of replicating retrovirus (Anwar et al., 2006). It has been suggested that linear RT oligonucleotides should contain at least 7 nucleotides of miRNA-specific sequence for efficient reverse transcription of mature miRNAs (Raymond et al., 2005). The poor discrimination of mature against pre-miRNAs by linear RT oligonucleotides (with 6 miRNA-specific nucleotides) used in this study, is likely to be due to the inefficient reverse transcription of mature miRNAs, consistent with the previous finding (Chen et al., 2005). These results suggested that the stem-loop secondary structure may stabilize the short base-pairing between RT oligonucleotide and the mature miRNA during reverse transcription.

MiRNAs are grouped into families (eg. let-7 family) based on identical seed sequence that spans 2-7 nucleotides at 5' of miRNAs, which is a critical determinant of target recognition (Lewis et al., 2005). Although miRNAs of the same family are likely to share some common targets and functions, specific members of the family may be involved in certain physiological processes and disease states. For instance, let-7b was found to be specifically up-regulated with age and responsible for the declined stem cell selfrenewal (Nishino et al., 2008). Low expression of let-7d was suggested as prognostic marker for head and neck squamous cell carcinoma (Childs et al., 2009), and let-7i was identified as a novel biomarker for human epithelial ovarian cancer (Yang et al., 2008). As such, specific and quantitative detection of these miRNAs is required for the development of biomarkers and for studies on the biogenesis of miRNAs. Previously, discrimination of let-7 homologs was achieved with TaqMan real-time RT-PCR assays, whereby after miRNA-specific RT, a common reverse primer was used for PCR and a miRNA-specific TaqMan probe was required for discrimination (Chen et al., 2005). Assays with similar strategy but without the use of fluorescent probes suffered from significantly poorer discrimination of the let-7 homologs (Raymond et al., 2005; Shi & Chiang, 2005; Sharbati-Tehrani et al., 2008). We hypothesized and showed that specificity of the assays can be dramatically enhanced by a hemi-nested miRNA-specific reverse PCR primer and do not require the use of fluorescent probe. Using this method, all the let-7 miRNAs can be specifically detected using inexpensive SYBR GREEN™ I, with excellent discrimination, comparable and in some cases, superior to the TaqMan real-time RTPCR (Chen et al., 2005).

The presence of excess RT oligonucleotides can serve as reverse primers during PCR, which will contribute to non-specific amplification. This is problematic especially when the forward primer in PCR can also hybridize to shared sequences (eg. cDNA from homologous miRNAs). A common practice to mitigate this problem is to reduce the carryover of RT oligonucleotides by diluting cDNA samples after RT. However, this approach will invariably reduce the assay sensitivity, especially with low abundance target miRNAs. For low abundance miRNAs, the assay is further improved by modifying the RT oligonucleotides with deoxyuridine residues and treating the cDNA with UDG prior to real-time PCR. UDG was first purified from $E.$ Coli and found able to cleave uracil from uracil-containing DNA (Lindahl et al., 1977). Release of uracil residues results in apyrimidinic sites on the DNA, which can block the replication by DNA polymerase during PCR (Longo et al., 1990). It is likely that UDG treatment disabled the unused dU RT oligonucleotides from serving as PCR primers. This is a simple and attractive approach in situations where maximum specificity is desired or discrimination is difficult to achieve during RT (eg. let-7a and let-7f share identical 3' sequences for RT priming).

It is known that miRNAs are differentially expressed in glioblastoma as compared to normal brain and many of these dysregulated miRNAs are involved in glioblastoma growth, invasion and chemoresistance (Lawler & Chiocca, 2009; Li et al., 2009). Using the hemi-nested real-time RT-PCR assays for selected miRNAs, GDNF was found to regulate the expressions of miR-7, miR-21, miR-218, let-7f, let-7g and let-7i through MEK-ERK1/2 MAPK signaling pathway. The functional significance of these GDNF-induced miRNAs remains to be investigated. Using the rapid and high throughput method developed herein, it is now feasible for drug screening by profiling changes in miRNA expression.

The number of miRNAs in the public domain currently is more than 17,000 (Kozomara & Griffiths-Jones, 2011) and expected to increase with both in silico prediction and in vivo validation such as deep sequencing. With the continuous demand for miRNA expression analysis, the hemi-nested real-time RT-PCR assay presented in this study provides a high performance method for the rapid and reliable detection of functional mature miRNAs.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. As used in this specification and the appended claims, all ranges or lists as given are intended to convey any intermediate value or range or any sublist contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

Ambros V, Lee R C, Lavanway A, Williams P T, Jewell D. 2003. MicroRNAs and other tiny endogenous RNAs in *C. elegans*. *Curr Biol* 13:807-818.

Anwar A, August J T, Too H P. 2006. A stem-loop-mediated reverse transcription realtime PCR for the selective detection and quantification of the replicative strand of an RNA virus. *Anal Biochem* 352:120-128.

Bar M, Wyman S K, Fritz B R, Qi J, Garg K S, Parkin R K, Kroh E M, Bendoraite A, Mitchell P S, Nelson A M, Ruzzo W L, Ware C, Radich J P, Gentleman R, Ruohola-Baker H, Tewari M. 2008. MicroRNA discovery and profiling in human embryonic stem cells by deep sequencing of small RNA libraries. *Stem Cells* 26:2496-2505.

Bartel D P. 2004. MicroRNAs: genomics, biogenesis, mechanism, and function. *Cell* 116:281-297.

Bartel D P. 2009. MicroRNAs: target recognition and regulatory functions. *Cell* 136:215-233.

Bissels U, Wild S, Tomiuk S, Holste A, Hafner M, Tuschl T, Bosio A. 2009. Absolute quantification of microRNAs by using a universal reference. *RNA*.

Calin G A, Liu C G, Sevignani C, Ferracin M, Felli N, Dumitru C D, Shimizu M, Cimmino A, Zupo S, Dono M, Dell'Aquila M L, Alder H, Rassenti L, Kipps T J, Bullrich F, Negrini M, Croce C M. 2004. MicroRNA profiling reveals distinct signatures in B cell chronic lymphocytic leukemias. *Proc Natl Acad Sci USA* 101:11755-11760.

Carthew R W. 2006. Gene regulation by microRNAs. *Curr Opin Genet Dev* 16:203-208.

Chen C, Ridzon D A, Broomer A J, Zhou Z, Lee D H, Nguyen J T, Barbisin M, Xu N L, Mahuvakar V R, Andersen M R, Lao K Q, Livak K J, Guegler K J. 2005. Realtime quantification of microRNAs by stem-loop RT-PCR. *Nucleic Acids Res* 33:e179.

Chen J F, Callis T E, Wang D Z. 2009a. microRNAs and muscle disorders. *J Cell Sci* 122:13-20.

Chen X, Ba Y, Ma L, Cai X, Yin Y, Wang K, Guo J, Zhang Y, Chen J, Guo X, Li Q, Li X, Wang W, Wang J, Jiang X, Xiang Y, Xu C, Zheng P, Zhang J, Li R, Zhang H, Shang X, Gong T, Ning G, Zen K, Zhang C Y. 2008. Characterization of microRNAs in serum: a novel class of biomarkers for diagnosis of cancer and other diseases. *Cell Res* 18:997-1006.

Chen Y, Gelfond J A, McManus L M, Shireman P K. 2009b. Reproducibility of quantitative RT-PCR array in miRNA expression profiling and comparison with microarray analysis. *BMC Genomics* 10:407.

Cheng Y, Zhang X, Li Z, Jiao X, Wang Y, Zhang Y. 2009. Highly sensitive determination of microRNA using target-primed and branched rolling-circle amplification. *Angew Chem Int Ed Engl* 48:3268-3272.

Childs G, Fazzari M, Kung G, Kawachi N, Brandwein-Gensler M, McLemore M, Chen Q, Burk R D, Smith R V, Prystowsky M B, Belbin T J, Schlecht N F. 2009. Low-level expression of microRNAs let-7d and miR-205 are prognostic markers of head and neck squamous cell carcinoma. *Am J Pathol* 174:736-745.

Duncan D D, Eshoo M, Esau C, Freier S M, Lollo B A. 2006. Absolute quantitation of microRNAs with a PCR-based assay. *Anal Biochem* 359:268-270.

Friedman R C, Farh K K, Burge C B, Bartel D P. 2009. Most mammalian mRNAs are conserved targets of microRNAs. *Genome Res* 19:92-105.

Goff L A, Davila J, Swerdel M R, Moore J C, Cohen R I, Wu H, Sun Y E, Hart R P. 2009. Ago2 immunoprecipitation identifies predicted microRNAs in human embryonic stem cells and neural precursors. *PLoS One* 4:e7192.

Guo M J, Hildbrand S, Leumann C J, McLaughlin L W and Waring M J. 1998. Inhibition of DNA polymerase reactions by pyrimidine nucleotide analogues lacking the 2-keto group. *Nucleic Acids Research*, 26(8): 1863-1869.

Harfe B D. 2005. MicroRNAs in vertebrate development. *Curr Opin Genet Dev* 15:410-415.

Hebert S S, De Strooper B. 2009. Alterations of the microRNA network cause neurodegenerative disease. *Trends Neurosci* 32:199-206.

Hunt E A, Goulding A M, Deo S K. 2009. Direct detection and quantification of microRNAs. *Anal Biochem.*

Jiang J, Lee E J, Gusev Y, Schmittgen T D. 2005. Real-time expression profiling of microRNA precursors in human cancer cell lines. *Nucleic Acids Res* 33:5394-5403.

Kozomara A, Griffiths-Jones S (2011) miRBase: integrating microRNA annotation and deep-sequencing data. *Nucleic acids research* 39 (Database issue), D152-57

Lawler S, Chiocca E A. 2009. Emerging functions of microRNAs in glioblastoma. *J Neurooncol* 92:297-306.

Lewis B P, Burge C B, Bartel D P. 2005. Conserved seed pairing, often flanked by adenosines, indicates that thousands of human genes are microRNA targets. *Cell* 120:15-20.

Li Y, Li W, Yang Y, Lu Y, He C, Hu G, Liu H, Chen J, He J, Yu H. 2009. MicroRNA-21 targets LRRFIP1 and contributes to VM-26 resistance in glioblastoma multiforme. *Brain Res* 1286:13-18.

Lindahl T, Ljungquist S, Siegert W, Nyberg B, Sperens B. 1977. DNA N-glycosidases: properties of uracil-DNA glycosidase from *Escherichia coli*. *J Biol Chem* 252:3286-3294.

Lindsay M A. 2008. microRNAs and the immune response. *Trends Immunol* 29:343-351.

Longo M C, Berninger M S, Hartley J L. 1990. Use of uracil DNA glycosylase to control carry-over contamination in polymerase chain reactions. *Gene* 93:125-128.

Mendes N D, Freitas A T, Sagot M F. 2009. Current tools for the identification of miRNA genes and their targets. *Nucleic Acids Res* 37:2419-2433.

Mestdagh P, Feys T, Bernard N, Guenther S, Chen C, Speleman F, Vandesompele J. 2008. High-throughput stem-loop RT-qPCR miRNA expression profiling using minute amounts of input RNA. *Nucleic Acids Res* 36:e143.

Michael M Z, SM OC, van Holst Pellekaan N G, Young G P, James R J. 2003. Reduced accumulation of specific microRNAs in colorectal neoplasia. *Mol Cancer Res* 1:882-891.

Miska E A. 2005: How microRNAs control cell division, differentiation and death. *Curr Opin Genet Dev* 15:563-568.

Mitchell P S, Parkin R K, Kroh E M, Fritz B R, Wyman S K, Pogosova-Agadjanyan E L, Peterson A, Noteboom J, O'Briant K C, Allen A, Lin D W, Urban N, Drescher C W, Knudsen B S, Stirewalt D L, Gentleman R, Vessella R L, Nelson P S, Martin D B, Tewari M. 2008. Circulating microRNAs as stable blood-based markers for cancer detection. *Proc Natl Acad Sci USA* 105:10513-10518.

Nishino J, Kim I, Chada K, Morrison S J. 2008. Hmga2 promotes neural stem cell selfrenewal in young but not old mice by reducing p16Ink4a and p19Arf Expression. *Cell* 135:227-239.

Pang J C, Kwok W K, Chen Z, Ng H K. 2009. Oncogenic role of microRNAs in brain tumors. *Acta Neuropathol* 117:599-611.

Raymond C K, Roberts B S, Garrett-Engele P, Lim L P, Johnson J M. 2005. Simple, quantitative primer-extension PCR assay for direct monitoring of microRNAs and short-interfering RNAs. *RNA* 11:1737-1744.

Schmittgen T D, Jiang J, Liu Q, Yang L. 2004. A high-throughput method to monitor the expression of microRNA precursors. *Nucleic Acids Res* 32:e43.

Schmittgen T D, Lee E J, Jiang J, Sarkar A, Yang L, Elton T S, Chen C. 2008. Realtime PCR quantification of precursor and mature microRNA. *Methods* 44:31-38.

Sharbati-Tehrani S, Kutz-Lohroff B, Bergbauer R, Scholven J, Einspanier R. 2008. miR-Q: a novel quantitative RT-PCR approach for the expression profiling of small RNA molecules such as miRNAs in a complex sample. *BMC Mol Biol* 9:34.

Shi R, Chiang V L. 2005. Facile means for quantifying microRNA expression by realtime PCR. *Biotechniques* 39:519-525.

Tang F, Hajkova P, Barton S C, Lao K, Surani M A. 2006. MicroRNA expression profiling of single whole embryonic stem cells. *Nucleic Acids Res* 34:e9.

Too H P. 2003. Real time PCR quantification of GFRalpha-2 alternatively spliced isoforms in murine brain and peripheral tissues. *Brain Res Mol Brain Res* 114:146-153.

Varkonyi-Gasic E, Wu R, Wood M, Walton E F, Hellens R P. 2007. Protocol: a highly sensitive RT-PCR method for detection and quantification of microRNAs. *Plant Methods* 3:12.

Visone R, Croce C M. 2009. MiRNAs and cancer. *Am J Pathol* 174:1131-1138. Wang H, Ach R A, Curry B. 2007. Direct and sensitive miRNA profiling from low-input total RNA. *RNA* 13:151-159.

Wulczyn F G, Smirnova L, Rybak A, Brandt C, Kwidzinski E, Ninnemann O, Strehle M, Seiler A, Schumacher S, Nitsch R. 2007. Post-transcriptional regulation of the let-7 microRNA during neural cell specification. *FASEB J* 21:415-426.

Yang H, Schmuke J J, Flagg L M, Roberts J K, Allen E M, Ivashuta S, Gilbertson L A, Armstrong T A, Christian A T. 2009. A novel real-time polymerase chain reaction method for high throughput quantification of small regulatory RNAs. *Plant Biotechnol J* 7:621-630.

Yang N, Kaur S, Volinia S, Greshock J, Lassus H, Hasegawa K, Liang S, Leminen A, Deng S, Smith L, Johnstone C N, Chen X M, Liu C G, Huang Q, Katsaros D, Calin G A, Weber B L, Butzow R, Croce C M, Coukos G, Zhang L. 2008. MicroRNA microarray identifies Let-7i as a novel biomarker and therapeutic target in human epithelial ovarian cancer. *Cancer Res* 68:10307-10314.

Yao B, Li J, Huang H, Sun C, Wang Z, Fan Y, Chang Q, Li S, Xi J. 2009. Quantitative analysis of zeptomole microRNAs based on isothermal ramification amplification. *RNA* 15:1787-1794.

What is claimed is:

1. A method for detecting a target RNA molecule in a sample, the method comprising:
reverse transcribing the target RNA contained in the sample using a reverse transcription (RT) oligonucleotide, the RT oligonucleotide comprising a stem-loop portion containing one or more nucleotides modifiable to block DNA polymerase extension and a target annealing portion that is complementary to a downstream portion of the target RNA, the target annealing portion located 3' to the stem-loop portion, to produce a reverse transcription product that comprises the RT oligonucleotide and a 3' extended region;
modifying the one or more modifiable nucleotides;
amplifying the reverse transcription product using (i) a first amplification primer that anneals to a downstream portion of the 3' extended region of the reverse transcription product and (ii) a second amplification primer that anneals to an interface portion of a DNA strand complementary to the reverse transcription product, the interface portion comprising a region that is complementary to a 3' portion of the RT oligonucleotide and a 5' portion of the 3' extended region in the reverse transcription product, to produce an amplification product; and
detecting the amplification product;
wherein the stem-loop portion adopts a stem-loop structure under conditions used for said reverse transcribing but does not adopt the stem-loop structure under conditions used for said amplifying and wherein the one or more nucleotides that are modifiable to block DNA polymerase extension comprise one or more ribonucleotides, and the modifying comprises treatment with an RNAse.

2. The method of claim 1, wherein the target RNA is an miRNA.

3. The method of claim 2, wherein the one or more nucleotides modifiable to block DNA polymerase extension is located within the loop of the stem-loop portion.

4. The method of claim 2, wherein the stem-loop portion further comprises one or more nucleotides modified to block DNA polymerase extension.

5. The method of claim 4, wherein the loop of the stem-loop portion comprises a nucleotide modified with an aliphatic carbon chain.

6. The method of claim 2, wherein the second amplification primer has a nucleotide that displays thermal stability when hybridized to DNA as the 3' terminal nucleotide.

7. The method of claim 6, wherein the nucleotide that displays thermal stability when hybridized to DNA is locked in an N-type furanose conformation.

8. The method of claim 2, wherein the distance in the sequence of the amplification product between the position of the 3' end of the first amplification primer when annealed to the reverse transcription product and the position of the 3' end of the second amplification primer when annealed to the DNA strand is from −4 to 5 nucleotides.

9. The method of claim 2, wherein the target annealing portion of the RT oligonucleotide is 5 to 15 nucleotides in length.

10. The method of claim 2, wherein the stem portion of the stem-loop is 4 to 6 nucleotides in length and the loop portion of the stem-loop is 4 to 12 nucleotides in length.

11. The method of claim 2, wherein the second amplification primer anneals to a sequence complementary to 13 to 24 nucleotides of the stem-loop portion of the RT oligonucleotide, 5 to 15 nucleotides of the target annealing portion of the RT oligonucleotide and 1 to 5 nucleotides at the 5' end of the 3' extended region of the reverse transcription product.

12. The method of claim 2, wherein the first amplification primer is 12 to 27 nucleotides in length.

13. The method of claim 2, wherein said detecting comprises detecting with a fluorescent intercalating dye.

14. The method of claim 13, wherein the fluorescent intercalating dye is SYBR GREEN™ (N',N'-dimethyl-N-[4-[(E)-(3-methyl-1,3-benzothiazol-2-ylidene)methyl]-1-phenylquinolin-1-ium-2-yl]-N-propylpropane-1,3-diamine).

15. A method for detecting a target RNA molecule in a sample, the method comprising:
reverse transcribing the target RNA contained in the sample using an RT oligonucleotide, the RT oligonucleotide comprising a stem-loop portion containing at least one dU nucleotide or a ribonucleotide and a target annealing portion that is complementary to a downstream portion of the target RNA, the stem portion of the stem-loop being 4 to 6 nucleotides in length and the loop portion of the stem-loop being 4 to 12 nucleotides in length, and the target annealing portion located 3' to the stem-loop portion and being 5 to 15 nucleotides in length, to produce a reverse transcription product that comprises the RT oligonucleotide and a 3' extended region;
modifying the dU nucleotide by treatment with uracil-DNA glycosylase or the ribonucleotide by treatment with an RNAse;
amplifying the reverse transcription product using (i) a first amplification primer that anneals to a downstream portion of the 3' extended region of the reverse transcription product and is 12 to 27 nucleotides in length, and (ii) a second amplification primer that anneals to an interface portion of a DNA strand complementary to the reverse transcription product, the interface portion comprising a region that is complementary to 13 to 24 nucleotides of the stem-loop portion of the RT oligonucleotide, 5 to 15 nucleotides of the target annealing portion of the RT oligonucleotide and 1 to 5 nucleotides at the 5' end of the 3' extended region of the reverse transcription product, to produce an amplification product in which the distance in the sequence of the amplification product between the position of the 3' end of the first amplification primer when annealed to the reverse transcription product and the position of the 3' end of the second amplification primer when annealed to the DNA strand is from −4 to 5 nucleotides; and detecting the amplification product;

wherein the stem-loop portion adopts a stem-loop structure under conditions used for said reverse transcribing but does not adopt the stem-loop structure under conditions used for said amplifying.

16. The method of claim 15, wherein the target RNA is an miRNA.

17. A method for detecting a target miRNA molecule in a sample, the method comprising:

reverse transcribing the target miRNA contained in the sample using an RT oligonucleotide, the RT oligonucleotide comprising a stem-loop portion containing a dU nucleotide and a target annealing portion that is complementary to a downstream portion of the target miRNA, the target annealing portion located 3' to the stem-loop portion, the stem portion of the stem-loop being 5 to 6 nucleotides in length and the loop portion of the stem-loop being 11 nucleotides in length, and the target annealing portion located 3' to the stem-loop portion and being 6 nucleotides in length, to produce a reverse transcription product that comprises the RT oligonucleotide and a 3' extended region;

modifying the dU nucleotide by treatment with uracil-DNA glycosylase;

amplifying the reverse transcription product using (i) a first amplification primer that anneals to a downstream portion of the 3' extended region of the reverse transcription product and is 21 nucleotides in length, and (ii) a second amplification primer that anneals to an interface portion of a DNA strand complementary to the reverse transcription product, the interface portion comprising a region that is complementary to 8 to 10 nucleotides of the stem-loop portion of the RT oligonucleotide, 6 nucleotides of the target annealing portion of the RT oligonucleotide and 3 to 5 nucleotides at the 5' end of the 3' extended region of the reverse transcription product, to produce an amplification product in which the distance in the sequence of the amplification product between the position of the 3' end of the first amplification primer when annealed to the reverse transcription product and the position of the 3' end of the second amplification primer when annealed to the DNA strand is from −2 to 2 nucleotides; and detecting the amplification product;

wherein the stem-loop portion adopts a stem-loop structure under conditions used for said reverse transcribing but does not adopt the stem-loop structure under conditions used for said amplifying.

18. The method of claim 15, wherein the stem-loop portion of the RT oligonucleotide contains dU nucleotide and modifying the du nucleotide by treatment with uracil-DNA glycosylase.

19. The method of claim 1, wherein the distance in the sequence of the amplification product between the position of the 3' end of the first amplification primer when annealed to the reverse transcription product and the position of the 3' end of the second amplification primer when annealed to the DNA strand is from −4 to 5 nucleotides; the target annealing portion of the RT oligonucleotide is 5 to 15 nucleotides in length; the stem portion of the stem-loop is 4 to 6 nucleotides in length and the loop portion of the stem-loop is 4 to 12 nucleotides in length; the second amplification primer anneals to a sequence complementary to 13 to 24 nucleotides of the stem-loop portion of the RT oligonucleotide, 5 to 15 nucleotides of the target annealing portion of the RT oligonucleotide and 1 to 5 nucleotides at the 5' end of the 3' extended region of the reverse transcription product; and the first amplification primer is 12 to 27 nucleotides in length.

* * * * *

SEQUENCE LISTING

```
<160> NUMBER OF SEQ ID NOS: 128

<210> SEQ ID NO 1
<211> LENGTH: 30
<212> TYPE: DNA
<213> ORGANISM: artificial
<220> FEATURE:
<223> OTHER INFORMATION: primer sequence

<400> SEQUENCE: 1
taatacgact cactataggg ttggatgttg                                30

<210> SEQ ID NO 2
<211> LENGTH: 21
<212> TYPE: DNA
<213> ORGANISM: artificial
<220> FEATURE:
<223> OTHER INFORMATION: primer sequence

<400> SEQUENCE: 2
ctgtagaggc atggcctgtg c                                         21

<210> SEQ ID NO 3
<211> LENGTH: 30
<212> TYPE: DNA
<213> ORGANISM: artificial
<220> FEATURE:
<223> OTHER INFORMATION: primer sequence

<400> SEQUENCE: 3
taatacgact cactataggg ctggatacag                                30

<210> SEQ ID NO 4
<211> LENGTH: 21
<212> TYPE: DNA
<213> ORGANISM: artificial
<220> FEATURE:
<223> OTHER INFORMATION: primer sequence

<400> SEQUENCE: 4
tgcgatggct ggcaccatta g                                         21

<210> SEQ ID NO 5
<211> LENGTH: 31
<212> TYPE: DNA
<213> ORGANISM: artificial
<220> FEATURE:
<223> OTHER INFORMATION: primer sequence

<400> SEQUENCE: 5
taatacgact cactataggg gtgataatgt a                              31

<210> SEQ ID NO 6
<211> LENGTH: 23
<212> TYPE: DNA
<213> ORGANISM: artificial
<220> FEATURE:
```

```
<223> OTHER INFORMATION: primer sequence

<400> SEQUENCE: 6
tgtagaaagc tgcgtgacgt tcc                                            23

<210> SEQ ID NO 7
<211> LENGTH: 30
<212> TYPE: DNA
<213> ORGANISM: artificial
<220> FEATURE:
<223> OTHER INFORMATION: primer sequence

<400> SEQUENCE: 7
taatacgact cactataggg gaccagtcgc                                     30

<210> SEQ ID NO 8
<211> LENGTH: 24
<212> TYPE: DNA
<213> ORGANISM: artificial
<220> FEATURE:
<223> OTHER INFORMATION: primer sequence

<400> SEQUENCE: 8
tgcaggagag cacggtgctt tccg                                           24

<210> SEQ ID NO 9
<211> LENGTH: 30
<212> TYPE: DNA
<213> ORGANISM: artificial
<220> FEATURE:
<223> OTHER INFORMATION: primer sequence

<400> SEQUENCE: 9
taatacgact cactataggt gtcgggtagc                                     30

<210> SEQ ID NO 10
<211> LENGTH: 20
<212> TYPE: DNA
<213> ORGANISM: artificial
<220> FEATURE:
<223> OTHER INFORMATION: primer sequence

<400> SEQUENCE: 10
tgtcagacag cccatcgact                                                20

<210> SEQ ID NO 11
<211> LENGTH: 30
<212> TYPE: DNA
<213> ORGANISM: artificial
<220> FEATURE:
<223> OTHER INFORMATION: primer sequence

<400> SEQUENCE: 11
taatacgact cactataggg tcagagtgag                                     30

<210> SEQ ID NO 12
<211> LENGTH: 33
<212> TYPE: DNA
<213> ORGANISM: artificial
<220> FEATURE:
<223> OTHER INFORMATION: primer sequence

<400> SEQUENCE: 12
tcagggaagg caatagattg tatagttatc tcc                                 33
```

```
<210> SEQ ID NO 13
<211> LENGTH: 30
<212> TYPE: DNA
<213> ORGANISM: artificial
<220> FEATURE:
<223> OTHER INFORMATION: primer sequence

<400> SEQUENCE: 13
taatacgact cactataggg tgtgggatga                                30

<210> SEQ ID NO 14
<211> LENGTH: 31
<212> TYPE: DNA
<213> ORGANISM: artificial
<220> FEATURE:
<223> OTHER INFORMATION: primer sequence

<400> SEQUENCE: 14
cgtgggaaag acagtagact gtatagttat c                              31

<210> SEQ ID NO 15
<211> LENGTH: 30
<212> TYPE: DNA
<213> ORGANISM: artificial
<220> FEATURE:
<223> OTHER INFORMATION: primer sequence

<400> SEQUENCE: 15
taatacgact cactataggg aggctgaggt                                30

<210> SEQ ID NO 16
<211> LENGTH: 25
<212> TYPE: DNA
<213> ORGANISM: artificial
<220> FEATURE:
<223> OTHER INFORMATION: primer sequence

<400> SEQUENCE: 16
tggcaaggca gtggcctgta cagtt                                     25

<210> SEQ ID NO 17
<211> LENGTH: 30
<212> TYPE: DNA
<213> ORGANISM: artificial
<220> FEATURE:
<223> OTHER INFORMATION: primer sequence

<400> SEQUENCE: 17
taatacgact cactataggg ctggctgagg                                30

<210> SEQ ID NO 18
<211> LENGTH: 30
<212> TYPE: DNA
<213> ORGANISM: artificial
<220> FEATURE:
<223> OTHER INFORMATION: primer sequence

<400> SEQUENCE: 18
tagcaaggca gtagcttgcg cagttatctc                                30

<210> SEQ ID NO 19
<211> LENGTH: 30
<212> TYPE: DNA
<213> ORGANISM: artificial
<220> FEATURE:
<223> OTHER INFORMATION: primer sequence
```

<400> SEQUENCE: 19
gctcagacag aagtcacact gagcaactat                                    30

<210> SEQ ID NO 20
<211> LENGTH: 18
<212> TYPE: DNA
<213> ORGANISM: artificial
<220> FEATURE:
<223> OTHER INFORMATION: primer sequence

<400> SEQUENCE: 20
gggcggtgag gtagtagg                                                 18

<210> SEQ ID NO 21
<211> LENGTH: 26
<212> TYPE: DNA
<213> ORGANISM: artificial
<220> FEATURE:
<223> OTHER INFORMATION: primer sequence

<400> SEQUENCE: 21
gaagtcacac tgagcaacta tacaac                                        26

<210> SEQ ID NO 22
<211> LENGTH: 30
<212> TYPE: DNA
<213> ORGANISM: artificial
<220> FEATURE:
<223> OTHER INFORMATION: primer sequence

<400> SEQUENCE: 22
gctcagacag aagtcacact gagcaaccac                                    30

<210> SEQ ID NO 23
<211> LENGTH: 21
<212> TYPE: DNA
<213> ORGANISM: artificial
<220> FEATURE:
<223> OTHER INFORMATION: primer sequence

<400> SEQUENCE: 23
cacactgagc aaccacacaa c                                             21

<210> SEQ ID NO 24
<211> LENGTH: 30
<212> TYPE: DNA
<213> ORGANISM: artificial
<220> FEATURE:
<223> OTHER INFORMATION: primer sequence

<400> SEQUENCE: 24
gctcagacag aagtcacact gagcaaccat                                    30

<210> SEQ ID NO 25
<211> LENGTH: 22
<212> TYPE: DNA
<213> ORGANISM: artificial
<220> FEATURE:
<223> OTHER INFORMATION: primer sequence

<400> SEQUENCE: 25
tcacactgag caaccataca ac                                            22

<210> SEQ ID NO 26
<211> LENGTH: 30

```
<212> TYPE: DNA
<213> ORGANISM: artificial
<220> FEATURE:
<223> OTHER INFORMATION: primer sequence

<400> SEQUENCE: 26
gctcagacag aagtcacact gagcactatg                              30

<210> SEQ ID NO 27
<211> LENGTH: 17
<212> TYPE: DNA
<213> ORGANISM: artificial
<220> FEATURE:
<223> OTHER INFORMATION: primer sequence

<400> SEQUENCE: 27
gcgggcggag aggtagt                                            17

<210> SEQ ID NO 28
<211> LENGTH: 22
<212> TYPE: DNA
<213> ORGANISM: artificial
<220> FEATURE:
<223> OTHER INFORMATION: primer sequence

<400> SEQUENCE: 28
gtcacactga gcactatgca ac                                      22

<210> SEQ ID NO 29
<211> LENGTH: 30
<212> TYPE: DNA
<213> ORGANISM: artificial
<220> FEATURE:
<223> OTHER INFORMATION: primer sequence

<400> SEQUENCE: 29
gctcagacag aagtcacact gagcactata                              30

<210> SEQ ID NO 30
<211> LENGTH: 16
<212> TYPE: DNA
<213> ORGANISM: artificial
<220> FEATURE:
<223> OTHER INFORMATION: primer sequence

<400> SEQUENCE: 30
cgggcggtga ggtagg                                             16

<210> SEQ ID NO 31
<211> LENGTH: 26
<212> TYPE: DNA
<213> ORGANISM: artificial
<220> FEATURE:
<223> OTHER INFORMATION: primer sequence

<400> SEQUENCE: 31
agaagtcaca ctgagcacta tacaac                                  26

<210> SEQ ID NO 32
<211> LENGTH: 19
<212> TYPE: DNA
<213> ORGANISM: artificial
<220> FEATURE:
<223> OTHER INFORMATION: primer sequence

<400> SEQUENCE: 32
```

-continued cgggcggtga ggtagtaga                                                19

<210> SEQ ID NO 33
<211> LENGTH: 27
<212> TYPE: DNA
<213> ORGANISM: artificial
<220> FEATURE:
<223> OTHER INFORMATION: primer sequence

<400> SEQUENCE: 33
agaagtcaca ctgagcaact atacaat                                       27

<210> SEQ ID NO 34
<211> LENGTH: 30
<212> TYPE: DNA
<213> ORGANISM: artificial
<220> FEATURE:
<223> OTHER INFORMATION: primer sequence

<400> SEQUENCE: 34
gctcagacag aagtcacact gagcactgta                                    30

<210> SEQ ID NO 35
<211> LENGTH: 19
<212> TYPE: DNA
<213> ORGANISM: artificial
<220> FEATURE:
<223> OTHER INFORMATION: primer sequence

<400> SEQUENCE: 35
cgggcggtga ggtagtagt                                                19

<210> SEQ ID NO 36
<211> LENGTH: 24
<212> TYPE: DNA
<213> ORGANISM: artificial
<220> FEATURE:
<223> OTHER INFORMATION: primer sequence

<400> SEQUENCE: 36
aagtcacact gagcactgta caaa                                          24

<210> SEQ ID NO 37
<211> LENGTH: 30
<212> TYPE: DNA
<213> ORGANISM: artificial
<220> FEATURE:
<223> OTHER INFORMATION: primer sequence

<400> SEQUENCE: 37
gctcagacag aagtcacact gagcacagca                                    30

<210> SEQ ID NO 38
<211> LENGTH: 19
<212> TYPE: DNA
<213> ORGANISM: artificial
<220> FEATURE:
<223> OTHER INFORMATION: primer sequence

<400> SEQUENCE: 38
cgggcggtga ggtagtagt                                                19

<210> SEQ ID NO 39
<211> LENGTH: 20
<212> TYPE: DNA
<213> ORGANISM: artificial

<220> FEATURE:
<223> OTHER INFORMATION: primer sequence

<400> SEQUENCE: 39
cacactgagc acagcacaaa                                              20

<210> SEQ ID NO 40
<211> LENGTH: 27
<212> TYPE: DNA
<213> ORGANISM: artificial
<220> FEATURE:
<223> OTHER INFORMATION: primer sequence

<400> SEQUENCE: 40
caccgttccc cgccgtcggt gctgttc                                      27

<210> SEQ ID NO 41
<211> LENGTH: 17
<212> TYPE: DNA
<213> ORGANISM: artificial
<220> FEATURE:
<223> OTHER INFORMATION: primer sequence

<400> SEQUENCE: 41
cccgcctggc tcagttc                                                 17

<210> SEQ ID NO 42
<211> LENGTH: 18
<212> TYPE: DNA
<213> ORGANISM: artificial
<220> FEATURE:
<223> OTHER INFORMATION: primer sequence

<400> SEQUENCE: 42
ccgtcggtgc tgttcctg                                                18

<210> SEQ ID NO 43
<211> LENGTH: 27
<212> TYPE: DNA
<213> ORGANISM: artificial
<220> FEATURE:
<223> OTHER INFORMATION: primer sequence

<400> SEQUENCE: 43
caccgttccc cgccgtcggt gcaggcc                                      27

<210> SEQ ID NO 44
<211> LENGTH: 19
<212> TYPE: DNA
<213> ORGANISM: artificial
<220> FEATURE:
<223> OTHER INFORMATION: primer sequence

<400> SEQUENCE: 44
cccgcctatt gcacttgtc                                               19

<210> SEQ ID NO 45
<211> LENGTH: 16
<212> TYPE: DNA
<213> ORGANISM: artificial
<220> FEATURE:
<223> OTHER INFORMATION: primer sequence

<400> SEQUENCE: 45
gtcggtgcag gccggg                                                  16

<210> SEQ ID NO 46
<211> LENGTH: 27
<212> TYPE: DNA
<213> ORGANISM: artificial
<220> FEATURE:
<223> OTHER INFORMATION: primer sequence

<400> SEQUENCE: 46
gaccgttccc cgccgtcggt ccacaaa                                          27

<210> SEQ ID NO 47
<211> LENGTH: 18
<212> TYPE: DNA
<213> ORGANISM: artificial
<220> FEATURE:
<223> OTHER INFORMATION: primer sequence

<400> SEQUENCE: 47
ccgccgtacc ctgtagaa                                                    18

<210> SEQ ID NO 48
<211> LENGTH: 18
<212> TYPE: DNA
<213> ORGANISM: artificial
<220> FEATURE:
<223> OTHER INFORMATION: primer sequence

<400> SEQUENCE: 48
cgtcggtcca caaattcg                                                    18

<210> SEQ ID NO 49
<211> LENGTH: 27
<212> TYPE: DNA
<213> ORGANISM: artificial
<220> FEATURE:
<223> OTHER INFORMATION: primer sequence

<400> SEQUENCE: 49
caccgttccc cgccgtcggt ggaaacc                                          27

<210> SEQ ID NO 50
<211> LENGTH: 19
<212> TYPE: DNA
<213> ORGANISM: artificial
<220> FEATURE:
<223> OTHER INFORMATION: primer sequence

<400> SEQUENCE: 50
cgggcagcta cattgtctg                                                   19

<210> SEQ ID NO 51
<211> LENGTH: 18
<212> TYPE: DNA
<213> ORGANISM: artificial
<220> FEATURE:
<223> OTHER INFORMATION: primer sequence

<400> SEQUENCE: 51
cgtcggtgga aaccagca                                                    18

<210> SEQ ID NO 52
<211> LENGTH: 27
<212> TYPE: DNA
<213> ORGANISM: artificial
<220> FEATURE:
<223> OTHER INFORMATION: primer sequence

<400> SEQUENCE: 52
caccgttccc cgccgtcggt gacccag					27

<210> SEQ ID NO 53
<211> LENGTH: 17
<212> TYPE: DNA
<213> ORGANISM: artificial
<220> FEATURE:
<223> OTHER INFORMATION: primer sequence

<400> SEQUENCE: 53
cgggcagcta catctgg					17

<210> SEQ ID NO 54
<211> LENGTH: 18
<212> TYPE: DNA
<213> ORGANISM: artificial
<220> FEATURE:
<223> OTHER INFORMATION: primer sequence

<400> SEQUENCE: 54
cgtcggtgac ccagtagc					18

<210> SEQ ID NO 55
<211> LENGTH: 27
<212> TYPE: DNA
<213> ORGANISM: artificial
<220> FEATURE:
<223> OTHER INFORMATION: primer sequence

<400> SEQUENCE: 55
caccgttccc cgccgtcggt gtcaaca					27

<210> SEQ ID NO 56
<211> LENGTH: 21
<212> TYPE: DNA
<213> ORGANISM: artificial
<220> FEATURE:
<223> OTHER INFORMATION: primer sequence

<400> SEQUENCE: 56
cccgcctagc ttatcagact g					21

<210> SEQ ID NO 57
<211> LENGTH: 19
<212> TYPE: DNA
<213> ORGANISM: artificial
<220> FEATURE:
<223> OTHER INFORMATION: primer sequence

<400> SEQUENCE: 57
gccgtcggtg tcaacatca					19

<210> SEQ ID NO 58
<211> LENGTH: 27
<212> TYPE: DNA
<213> ORGANISM: artificial
<220> FEATURE:
<223> OTHER INFORMATION: primer sequence

<400> SEQUENCE: 58
caccgttccg cgccgtcggt gctcggg					27

<210> SEQ ID NO 59

```
<211> LENGTH: 19
<212> TYPE: DNA
<213> ORGANISM: artificial
<220> FEATURE:
<223> OTHER INFORMATION: primer sequence

<400> SEQUENCE: 59
cgccgtcctg tactgagct                                               19

<210> SEQ ID NO 60
<211> LENGTH: 17
<212> TYPE: DNA
<213> ORGANISM: artificial
<220> FEATURE:
<223> OTHER INFORMATION: primer sequence

<400> SEQUENCE: 60
gtcggtgctc ggggcag                                                 17

<210> SEQ ID NO 61
<211> LENGTH: 27
<212> TYPE: DNA
<213> ORGANISM: artificial
<220> FEATURE:
<223> OTHER INFORMATION: primer sequence

<400> SEQUENCE: 61
cacggaaccc cgccgaccgt gaactca                                      27

<210> SEQ ID NO 62
<211> LENGTH: 18
<212> TYPE: DNA
<213> ORGANISM: artificial
<220> FEATURE:
<223> OTHER INFORMATION: primer sequence

<400> SEQUENCE: 62
cgccgaaacc gttaccat                                                18

<210> SEQ ID NO 63
<211> LENGTH: 21
<212> TYPE: DNA
<213> ORGANISM: artificial
<220> FEATURE:
<223> OTHER INFORMATION: primer sequence

<400> SEQUENCE: 63
gccgaccgtg aactcagtaa t                                            21

<210> SEQ ID NO 64
<211> LENGTH: 27
<212> TYPE: DNA
<213> ORGANISM: artificial
<220> FEATURE:
<223> OTHER INFORMATION: primer sequence

<400> SEQUENCE: 64
caccgttccc cgccgtcggt gtgtaaa                                      27

<210> SEQ ID NO 65
<211> LENGTH: 18
<212> TYPE: DNA
<213> ORGANISM: artificial
<220> FEATURE:
<223> OTHER INFORMATION: primer sequence

<400> SEQUENCE: 65
```

-continued

```
ccgccgtagc agcacatc                                                18

<210> SEQ ID NO 66
<211> LENGTH: 20
<212> TYPE: DNA
<213> ORGANISM: artificial
<220> FEATURE:
<223> OTHER INFORMATION: primer sequence

<400> SEQUENCE: 66
ccgtcggtgt gtaaaccatg                                              20

<210> SEQ ID NO 67
<211> LENGTH: 27
<212> TYPE: DNA
<213> ORGANISM: artificial
<220> FEATURE:
<223> OTHER INFORMATION: primer sequence

<400> SEQUENCE: 67
caccgttccc cgccgtcggt gagccta                                      27

<210> SEQ ID NO 68
<211> LENGTH: 19
<212> TYPE: DNA
<213> ORGANISM: artificial
<220> FEATURE:
<223> OTHER INFORMATION: primer sequence

<400> SEQUENCE: 68
cgggcgtgag aactgaatt                                               19

<210> SEQ ID NO 69
<211> LENGTH: 18
<212> TYPE: DNA
<213> ORGANISM: artificial
<220> FEATURE:
<223> OTHER INFORMATION: primer sequence

<400> SEQUENCE: 69
cgtcggtgag cctatgga                                                18

<210> SEQ ID NO 70
<211> LENGTH: 27
<212> TYPE: DNA
<213> ORGANISM: artificial
<220> FEATURE:
<223> OTHER INFORMATION: primer sequence

<400> SEQUENCE: 70
cacggaaccc cgccgaccgt gaaagag                                      27

<210> SEQ ID NO 71
<211> LENGTH: 17
<212> TYPE: DNA
<213> ORGANISM: artificial
<220> FEATURE:
<223> OTHER INFORMATION: primer sequence

<400> SEQUENCE: 71
ggcgtcacag tgaaccg                                                 17

<210> SEQ ID NO 72
<211> LENGTH: 18
<212> TYPE: DNA
```

```
<213> ORGANISM: artificial
<220> FEATURE:
<223> OTHER INFORMATION: primer sequence

<400> SEQUENCE: 72
cgaccgtgaa agagaccg                                                 18

<210> SEQ ID NO 73
<211> LENGTH: 27
<212> TYPE: DNA
<213> ORGANISM: artificial
<220> FEATURE:
<223> OTHER INFORMATION: primer sequence

<400> SEQUENCE: 73
cacggaaccc cgccgaccgt gactcac                                       27

<210> SEQ ID NO 74
<211> LENGTH: 18
<212> TYPE: DNA
<213> ORGANISM: artificial
<220> FEATURE:
<223> OTHER INFORMATION: primer sequence

<400> SEQUENCE: 74
ccgccgaaca ttcaacct                                                 18

<210> SEQ ID NO 75
<211> LENGTH: 18
<212> TYPE: DNA
<213> ORGANISM: artificial
<220> FEATURE:
<223> OTHER INFORMATION: primer sequence

<400> SEQUENCE: 75
cgaccgtgac tcaccgac                                                 18

<210> SEQ ID NO 76
<211> LENGTH: 17
<212> TYPE: DNA
<213> ORGANISM: artificial
<220> FEATURE:
<223> OTHER INFORMATION: primer sequence

<400> SEQUENCE: 76
cgccgaacat tcaacgc                                                  17

<210> SEQ ID NO 77
<211> LENGTH: 27
<212> TYPE: DNA
<213> ORGANISM: artificial
<220> FEATURE:
<223> OTHER INFORMATION: primer sequence

<400> SEQUENCE: 77
cacggaaccc cgccgaccgt gacccac                                       27

<210> SEQ ID NO 78
<211> LENGTH: 18
<212> TYPE: DNA
<213> ORGANISM: artificial
<220> FEATURE:
<223> OTHER INFORMATION: primer sequence

<400> SEQUENCE: 78
ccgccgaaca ttcattgc                                                 18
```

<210> SEQ ID NO 79
<211> LENGTH: 17
<212> TYPE: DNA
<213> ORGANISM: artificial
<220> FEATURE:
<223> OTHER INFORMATION: primer sequence

<400> SEQUENCE: 79
gaccgtgacc caccgac                                                    17

<210> SEQ ID NO 80
<211> LENGTH: 27
<212> TYPE: DNA
<213> ORGANISM: artificial
<220> FEATURE:
<223> OTHER INFORMATION: primer sequence

<400> SEQUENCE: 80
gaccgttccc cgccgtcggt ctcaacg                                         27

<210> SEQ ID NO 81
<211> LENGTH: 19
<212> TYPE: DNA
<213> ORGANISM: artificial
<220> FEATURE:
<223> OTHER INFORMATION: primer sequence

<400> SEQUENCE: 81
gggcgaatga cacgatcac                                                  19

<210> SEQ ID NO 82
<211> LENGTH: 18
<212> TYPE: DNA
<213> ORGANISM: artificial
<220> FEATURE:
<223> OTHER INFORMATION: primer sequence

<400> SEQUENCE: 82
cgtcggtctc aacgggag                                                   18

<210> SEQ ID NO 83
<211> LENGTH: 27
<212> TYPE: DNA
<213> ORGANISM: artificial
<220> FEATURE:
<223> OTHER INFORMATION: primer sequence

<400> SEQUENCE: 83
caccgttccc cgccgtcggt gacaaca                                         27

<210> SEQ ID NO 84
<211> LENGTH: 20
<212> TYPE: DNA
<213> ORGANISM: artificial
<220> FEATURE:
<223> OTHER INFORMATION: primer sequence

<400> SEQUENCE: 84
cgccctggaa gactagtgat                                                 20

<210> SEQ ID NO 85
<211> LENGTH: 19
<212> TYPE: DNA
<213> ORGANISM: artificial
<220> FEATURE:

```
<223> OTHER INFORMATION: primer sequence

<400> SEQUENCE: 85
ccgtcggtga caacaaaat                                          19

<210> SEQ ID NO 86
<211> LENGTH: 27
<212> TYPE: DNA
<213> ORGANISM: artificial
<220> FEATURE:
<223> OTHER INFORMATION: primer sequence

<400> SEQUENCE: 86
caccgttccg cgccgtcggt gggcatt                                 27

<210> SEQ ID NO 87
<211> LENGTH: 18
<212> TYPE: DNA
<213> ORGANISM: artificial
<220> FEATURE:
<223> OTHER INFORMATION: primer sequence

<400> SEQUENCE: 87
catacctaag gcacgcgg                                           18

<210> SEQ ID NO 88
<211> LENGTH: 17
<212> TYPE: DNA
<213> ORGANISM: artificial
<220> FEATURE:
<223> OTHER INFORMATION: primer sequence

<400> SEQUENCE: 88
gtcggtgggc attcacc                                            17

<210> SEQ ID NO 89
<211> LENGTH: 27
<212> TYPE: DNA
<213> ORGANISM: artificial
<220> FEATURE:
<223> OTHER INFORMATION: primer sequence

<400> SEQUENCE: 89
caccgttccc cgccgtcggt gctacgc                                 27

<210> SEQ ID NO 90
<211> LENGTH: 20
<212> TYPE: DNA
<213> ORGANISM: artificial
<220> FEATURE:
<223> OTHER INFORMATION: primer sequence

<400> SEQUENCE: 90
ccgccgttat tgcttaagaa                                         20

<210> SEQ ID NO 91
<211> LENGTH: 18
<212> TYPE: DNA
<213> ORGANISM: artificial
<220> FEATURE:
<223> OTHER INFORMATION: primer sequence

<400> SEQUENCE: 91
cgtcggtgct acgcgtat                                           18
```

-continued

<210> SEQ ID NO 92
<211> LENGTH: 27
<212> TYPE: DNA
<213> ORGANISM: artificial
<220> FEATURE:
<223> OTHER INFORMATION: primer sequence

<400> SEQUENCE: 92
caccgttccc cgccgtcggt gctggag                27

<210> SEQ ID NO 93
<211> LENGTH: 19
<212> TYPE: DNA
<213> ORGANISM: artificial
<220> FEATURE:
<223> OTHER INFORMATION: primer sequence

<400> SEQUENCE: 93
ccgcctctac agtgcacgt                19

<210> SEQ ID NO 94
<211> LENGTH: 18
<212> TYPE: DNA
<213> ORGANISM: artificial
<220> FEATURE:
<223> OTHER INFORMATION: primer sequence

<400> SEQUENCE: 94
cgtcggtgct ggagacac                18

<210> SEQ ID NO 95
<211> LENGTH: 27
<212> TYPE: DNA
<213> ORGANISM: artificial
<220> FEATURE:
<223> OTHER INFORMATION: primer sequence

<400> SEQUENCE: 95
caccgttccc cgccgtcggt gacatgg                27

<210> SEQ ID NO 96
<211> LENGTH: 19
<212> TYPE: DNA
<213> ORGANISM: artificial
<220> FEATURE:
<223> OTHER INFORMATION: primer sequence

<400> SEQUENCE: 96
tcgggcttgt gcttgatct                19

<210> SEQ ID NO 97
<211> LENGTH: 19
<212> TYPE: DNA
<213> ORGANISM: artificial
<220> FEATURE:
<223> OTHER INFORMATION: primer sequence

<400> SEQUENCE: 97
ccgtcggtga catggttag                19

<210> SEQ ID NO 98
<211> LENGTH: 27
<212> TYPE: DNA
<213> ORGANISM: artificial
<220> FEATURE:
<223> OTHER INFORMATION: primer sequence

```
<400> SEQUENCE: 98
caccgttccc cgccgtcggt gtcaaca                                27

<210> SEQ ID NO 99
<211> LENGTH: 27
<212> TYPE: DNA
<213> ORGANISM: artificial
<220> FEATURE:
<223> OTHER INFORMATION: primer sequence

<400> SEQUENCE: 99
gacccttcgc ggccgtcggt gtcaaca                                27

<210> SEQ ID NO 100
<211> LENGTH: 27
<212> TYPE: DNA
<213> ORGANISM: artificial
<220> FEATURE:
<223> OTHER INFORMATION: primer sequence

<400> SEQUENCE: 100
caccgttccc cgccgtcggt gacaaca                                27

<210> SEQ ID NO 101
<211> LENGTH: 27
<212> TYPE: DNA
<213> ORGANISM: artificial
<220> FEATURE:
<223> OTHER INFORMATION: primer sequence

<400> SEQUENCE: 101
gacccttcgc ggccgtcggt gacaaca                                27

<210> SEQ ID NO 102
<211> LENGTH: 27
<212> TYPE: DNA
<213> ORGANISM: artificial
<220> FEATURE:
<223> OTHER INFORMATION: primer sequence

<400> SEQUENCE: 102
caccgttccc cgccgtcggt gacatgg                                27

<210> SEQ ID NO 103
<211> LENGTH: 27
<212> TYPE: DNA
<213> ORGANISM: artificial
<220> FEATURE:
<223> OTHER INFORMATION: primer sequence

<400> SEQUENCE: 103
gacccttcgc ggccgtcggt gacatgg                                27

<210> SEQ ID NO 104
<211> LENGTH: 30
<212> TYPE: DNA
<213> ORGANISM: artificial
<220> FEATURE:
<223> OTHER INFORMATION: primer sequence

<400> SEQUENCE: 104
gctcagacag aagtcacact gagcaactat                             30

<210> SEQ ID NO 105
<211> LENGTH: 30
```

<212> TYPE: DNA
<213> ORGANISM: artificial
<220> FEATURE:
<223> OTHER INFORMATION: primer sequence

<400> SEQUENCE: 105
cgagagtcag aagtcacact gagcaactat                                30

<210> SEQ ID NO 106
<211> LENGTH: 30
<212> TYPE: DNA
<213> ORGANISM: artificial
<220> FEATURE:
<223> OTHER INFORMATION: primer sequence

<400> SEQUENCE: 106
gctcagacag aagtcacact gagcactgta                                30

<210> SEQ ID NO 107
<211> LENGTH: 30
<212> TYPE: DNA
<213> ORGANISM: artificial
<220> FEATURE:
<223> OTHER INFORMATION: primer sequence

<400> SEQUENCE: 107
cgagagtcag aagtcacact gagcactgta                                30

<210> SEQ ID NO 108
<211> LENGTH: 30
<212> TYPE: DNA
<213> ORGANISM: artificial
<220> FEATURE:
<223> OTHER INFORMATION: primer sequence

<400> SEQUENCE: 108
gctcagacag aagtcacact gagcacagca                                30

<210> SEQ ID NO 109
<211> LENGTH: 30
<212> TYPE: DNA
<213> ORGANISM: artificial
<220> FEATURE:
<223> OTHER INFORMATION: primer sequence

<400> SEQUENCE: 109
cgagagtcag aagtcacact gagcacagca                                30

<210> SEQ ID NO 110
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miRNA sequence

<400> SEQUENCE: 110
uagcuuauca gacugauguu ga                                        22

<210> SEQ ID NO 111
<211> LENGTH: 22
<212> TYPE: DNA
<213> ORGANISM: artificial
<220> FEATURE:
<223> OTHER INFORMATION: primer sequence

```
<400> SEQUENCE: 111
tcaacatcag tctgataagc ta                                            22

<210> SEQ ID NO 112
<211> LENGTH: 22
<212> TYPE: DNA
<213> ORGANISM: artificial
<220> FEATURE:
<223> OTHER INFORMATION: primer sequence

<400> SEQUENCE: 112
tagcttatca gactgatgtt ga                                            22

<210> SEQ ID NO 113
<211> LENGTH: 27
<212> TYPE: DNA
<213> ORGANISM: artificial
<220> FEATURE:
<223> OTHER INFORMATION: primer sequence

<400> SEQUENCE: 113
caccgttccc cgccgtcggt gtcaaca                                       27

<210> SEQ ID NO 114
<211> LENGTH: 21
<212> TYPE: DNA
<213> ORGANISM: artificial
<220> FEATURE:
<223> OTHER INFORMATION: primer sequence

<400> SEQUENCE: 114
cccgcctagc ttatcagact g                                             21

<210> SEQ ID NO 115
<211> LENGTH: 19
<212> TYPE: DNA
<213> ORGANISM: artificial
<220> FEATURE:
<223> OTHER INFORMATION: primer sequence

<400> SEQUENCE: 115
gccgtcggtg tcaacatca                                                19

<210> SEQ ID NO 116
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: let-7a miRNA sequence

<400> SEQUENCE: 116
ugagguagua gguuguauag uu                                            22

<210> SEQ ID NO 117
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: let-7b miRNA sequence

<400> SEQUENCE: 117
ugagguagua gguugugugg uu                                            22
```

```
<210> SEQ ID NO 118
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: let-7c miRNA sequence

<400> SEQUENCE: 118
ugagguagua gguuguaugg uu                                              22

<210> SEQ ID NO 119
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: let-7f miRNA sequence

<400> SEQUENCE: 119
ugagguagua gauuguauag uu                                              22

<210> SEQ ID NO 120
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: let-7g miRNA sequence

<400> SEQUENCE: 120
ugagguagua guuuguacag u                                               21

<210> SEQ ID NO 121
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: let-7i miRNA sequence

<400> SEQUENCE: 121
ugagguagua guuugugcug u                                               21

<210> SEQ ID NO 122
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: let-7d miRNA sequence

<400> SEQUENCE: 122
agagguagua gguugcauag u                                               21

<210> SEQ ID NO 123
<211> LENGTH: 21
<212> TYPE: RNA
<213> ORGANISM: Homo sapiens
<220> FEATURE:
<221> NAME/KEY: misc_feature
<222> LOCATION: (1)..(21)
```

<223> OTHER INFORMATION: let-7e miRNA sequence

<400> SEQUENCE: 123
ugagguagga gguuguauag u                                            21

<210> SEQ ID NO 124
<211> LENGTH: 30
<212> TYPE: DNA
<213> ORGANISM: artificial
<220> FEATURE:
<223> OTHER INFORMATION: primer sequence

<400> SEQUENCE: 124
gctcagacag aagtcacact gagcaactat                                   30

<210> SEQ ID NO 125
<211> LENGTH: 30
<212> TYPE: DNA
<213> ORGANISM: artificial
<220> FEATURE:
<223> OTHER INFORMATION: primer sequence
<220> FEATURE:
<221> NAME/KEY: misc_feature
<222> LOCATION: (14)..(14)
<223> OTHER INFORMATION: position 14 is dU

<400> SEQUENCE: 125
gctcagacag aagucacact gagcaactat                                   30

<210> SEQ ID NO 126
<211> LENGTH: 30
<212> TYPE: DNA
<213> ORGANISM: artificial
<220> FEATURE:
<223> OTHER INFORMATION: primer sequence
<220> FEATURE:
<221> NAME/KEY: misc_feature
<222> LOCATION: (20)..(20)
<223> OTHER INFORMATION: position 20 is dU

<400> SEQUENCE: 126
gctcagacag aagtcacacu gagcaactat                                   30

<210> SEQ ID NO 127
<211> LENGTH: 24
<212> TYPE: DNA
<213> ORGANISM: artificial
<220> FEATURE:
<223> OTHER INFORMATION: primer sequence

<400> SEQUENCE: 127
caccgttttc tttcggtgtc aaca                                         24

<210> SEQ ID NO 128
<211> LENGTH: 24
<212> TYPE: DNA
<213> ORGANISM: artificial
<220> FEATURE:
<223> OTHER INFORMATION: primer sequence
<220> FEATURE:
<221> NAME/KEY: misc_feature
<222> LOCATION: (6)..(9)

```
<223> OTHER INFORMATION: positions 6 to 9 are dU
<220> FEATURE:
<221> NAME/KEY: misc_feature
<222> LOCATION: (11)..(13)
<223> OTHER INFORMATION: positions 11 to 13 are dU

<400> SEQUENCE: 128
caccguuuuc uuucggtgtc aaca                                              24
```